US009868762B2

(12) United States Patent
Demina et al.

(10) Patent No.: US 9,868,762 B2
(45) Date of Patent: Jan. 16, 2018

(54) METHOD FOR PURIFYING VIRUS-LIKE PARTICLES (VLP)

(75) Inventors: Victoria Demina, Bonn (DE); Heiko Manninga, Bonn (DE)

(73) Assignee: LIFE SCIENCE INKUBATOR BETRIEBS GMBH & CO. KG, Bonn (DE)

( * ) Notice: Subject to any disclaimer, the term of this patent is extended or adjusted under 35 U.S.C. 154(b) by 0 days.

(21) Appl. No.: 14/236,210

(22) PCT Filed: Aug. 1, 2012

(86) PCT No.: PCT/EP2012/003273
§ 371 (c)(1),
(2), (4) Date: Apr. 17, 2014

(87) PCT Pub. No.: WO2013/017272
PCT Pub. Date: Feb. 7, 2013

(65) Prior Publication Data
US 2014/0309408 A1 Oct. 16, 2014

(30) Foreign Application Priority Data
Aug. 2, 2011 (EP) .................................. 11176295

(51) Int. Cl.
C07K 1/34 (2006.01)
C07K 14/025 (2006.01)
C07K 1/18 (2006.01)
C07K 14/005 (2006.01)
C12N 7/00 (2006.01)
C07K 1/22 (2006.01)
C07K 14/00 (2006.01)
A61K 39/00 (2006.01)

(52) U.S. Cl.
CPC ............. C07K 1/34 (2013.01); C07K 1/22 (2013.01); C07K 14/00 (2013.01); C07K 14/005 (2013.01); C12N 7/00 (2013.01); A61K 2039/5258 (2013.01); C12N 2710/22023 (2013.01); C12N 2710/22051 (2013.01)

(58) Field of Classification Search
None
See application file for complete search history.

(56) References Cited

U.S. PATENT DOCUMENTS

| 5,534,257 A | 7/1996 | Mastico et al. |
| 2009/0048433 A1 | 2/2009 | Richter et al. |
| 2010/0150961 A1* | 6/2010 | Vedvick et al. ........... 424/216.1 |

FOREIGN PATENT DOCUMENTS

| EP | 1270586 B1 | 1/2003 |
| EP | 2133358 A1 | 12/2009 |
| WO | WO 92/13081 A1 | 8/1992 |
| WO | 97/19174 A1 | 5/1997 |
| WO | WO 2006/136566 A1 | 12/2006 |

OTHER PUBLICATIONS

Hensgen et al. Purification of Minute Virus of Mice using High Performance Tangential Flow Filtration, Desalination 250 (2010) p. 1121-1124. Available online Oct. 13, 2009.*
Goldmann et al. Molecular Cloning and Expression of Major Structural Protein VP1 of the Human Polyomavirus JC Virus: ormation of Virus-Like Particles Useful for Immunological and Therapeutic Studies. Journal of Virology, May 1999, p. 4465-4469 vol. 73, No. 5.*
GenBank: AAC59325.1. VP1 [JC polyomavirus], dated Apr. 13, 1998.*
Kosukegawa et al. Purification and characterization of virus-like particles and pentamers produced by the expression of SV40 capsid proteins in insect cells. Biochim Biophys Acta. May 21, 1996;1290(1):37-45.*
Negrete et al. Use of hollow fiber tangential flow filtration for the recovery and concentration of HIV virus-like particles produced in insect cells. Journal of Virological Methods 195 (2014) 240-246.*
Cook et al. Purification of virus-like particles of recombinant human papillomavirus type 11 major capsid protein L1 from *Saccharomyces cerevisiae*. Protein Expr Purif. Dec. 1999;17(3):477-84.*
Spectrumlabs.com, "Laboratory Dialysis Frequently Asked Questions," retrieved online at: http://www.spectrumlabs.com/dialysis/FAQ.html, 4 pages (2012).
International Preliminary Report on Patentability and Written Opinion for Application No. PCT/EP2012/003273, 13 pages, dated Feb. 4, 2014.
C. Goldmann et al.: "Molecular Cloning and Expression of Major Structural Protein VP1 of the Human Polyomavirus JC Virus: Formation of Virus-Like Particles Useful for Immunological and Therapeutic Studies", Journal of Virology, vol. 73, No. 5, pp. 4465-4469 (1999).
P. Pushko et al.: "Analysis of RNA phage *fr* coat protein assembly by insertion, deletion and substitution mutagenesis", Protein Engineering, vol. 6, No. 8, pp. 883-891 (1993).
"Ultrafiltration Fundamentals: Background; Choosing the Correct Device; Choosing the Correct MWCO", http://www.pall.com/contact, pp. 1-4.
H. Rehm: "Der Experimentalor: Proleinbiochemie/Proteomics", 4th revised edition; Spektrum Academic Pubisher Heidelberg, English Translation, pp. 1-2 (2006).

(Continued)

*Primary Examiner* — Nianxiang (Nick) Zou
(74) *Attorney, Agent, or Firm* — Norman B. Thot

(57) ABSTRACT

The invention relates to a method for purifying compositions containing virus-like particles (VLP), wherein a VLP-containing composition is filtered through a filter medium, in particular through a membrane, having a molecular weight cut off (MWCO) of more than 30 kDa, and the cell culture supernatant of VLP-expressing cells is used as a VLP-containing composition. The invention further relates to a VLP-containing composition which can be produced by this method.

14 Claims, 7 Drawing Sheets

(56) References Cited

OTHER PUBLICATIONS

D. H. Atha et al.: "Mechanism of Precipitation of Proteins by Polyethylene Glycols", The Journal of Biological Chemistry, vol. 256, No. 23, pp. 12108-12117 (1981).

Citkowicz, A. et al., "Characterization of virus-like particle assembly for DNA delivery using asymmetrical flow field-flow fractionation and light scattering," Anal. Biochem., vol. 376(2):163-172 (2008).

Kim, Mikyung et al., "Immunogenicity of recombinant human immunodeficiency virus type 1-like particles expressing gp41 derivatives in a pre-fusion state," Vaccine, vol. 25(27):5102-5114 (2007).

Leb, Victoria M. et al., "Modulation of allergen-specific T-lymphocyte function by virus-like particles decorated with HLA class II molecules," J. Allergy Clin. Immunol., vol. 124:121-128 (2009).

Palomares, Laura A. et al., "Challenges for the production of virus-like particles in insect cells: The case of rotavirus-like particles," Biochemical Engineering Journal, vol. 45(3):158-167 (2009).

Peixoto, C. et al., "Downstream processing of triple layered rotavirus like particles," J. Biotechnol., vol. 127(3):452-461 (2007).

Santi, Luca et al., "An efficient plant viral expression system generating orally immunogenic Norwalk virus-like particles," Vaccine, vol. 26(15):1846-1854 (2008).

Volpers, C. et al., "Assembly of the major and the minor capsid protein of human papillomavirus type 33 into virus-like particles and tubular structures in insect cells," Virology, vol. 200(2):504-512 (1994).

Wang, T. et al., "Interaction with 7SL RNA but not with HIV-1 genomic RNA or P bodies is required for APOBEC3F virion packaging," J. Mol. Biol., vol. 375(4):1098-1112 (2008).

International Search Report for Application No. PCT/EP2012/003273, 5 pages, dated Dec. 21, 2012.

A. Saxena et al.: "Membrane-based techniques for the seperation and purification of proteins: An overview", Advances in Colloid and Interface Science, vol. 145, pp. 1-22 (2009).

* cited by examiner

Figure 1

| Process for producing the baculoviruses |
|---|
| Thawing the frozen SF9 cells at 26°C for 2-5 min.  Culturing the cells (T175 T-flask) Seeding 3-5 x $10^5$ cells/ml in 30 ml of cell culture medium  Culturing the cells to a cell density (vital) of 0.6 to 1.0 x $10^6$ cells/ml  Depositing the cells in 6-well plates Seeding 9 x $10^5$ cells/well in 2 ml TC100/10% FCS/1% penicillin/streptomycin Culturing the cells for 12-24 hours  Change of medium Incubating the cells with DNA-Cellfectin-precipitates for 5 hours at 26°C  Change of medium 2 ml TC 100/10% FCS/1% Culturing the cells for 3-5 days at 26°C  Virus harvest (see flow diagram in figure 2) |

Figure 5

| VLP production method: Part 3a – Purification of the VLPs by dissociation and chromatography with a weak anion exchanger |
|---|
| Dissociation of the VLPs with 5 mM DTT and 10 mM EDTA for 1 hour at room temperature |
|  |
| Purifying the VP1 pentamers by anion-exchange chromatography with DEAE matrix. VP1 pentamers are eluted with 500 mM NaCl |
|  |
| Dialysis against physiological saline at 5 ± 3 °C overnight |
|  |
| Mixing the VP1 pentamers with active ingredient(s) |
|  |
| Dialysis against reassociation buffer (1-5 mM CaCl$_2$, 10 mM Tris-HCl, 150 mM NaCl, pH 7.5) at 5 ± 3 °

Figure 6

| VLP production method: |
|---|
| Part 3b – Purifying the VLPs by dissociation and chromatography using a strong anion exchanger |
| Dissociation of the VLPs with 5 to 20 mM DTT and 10 to 30 mM EDTA for 1 hour at room temperature |

Purifying the VP1 pentamers by anion-exchanger chromatography (MonoQ column or Q-Sepharose). VP1 pentamers are eluted with 300 mM NaCl.

Mixing the VP1 pentamers with active ingredient(s)

Dialysis against reassociation buffer (1 to 5 mM $CaCl_2$, 10 mM Tris-HCl, 150 mM NaCl, pH 7.5) at 5 ± 3°C over 24-48 h

↓

Storing the active ingredient-carrying VP1-VLPs at 5 ± 3°C until further processing or long-term storage at -80°C

Figure 7

```
   1  CCTATAAATATTCCGGATTATTCATACCGTCCCACCATCGGGCGCGGATCCGCCACCATG
                                                                  M__

61  GCTCCCACCAAGCGCAAGGGCGAGCCCAAGGACCCCGTGCAAGTGCCCAAGCTGCTGATC
      A__P__T__K__R__K__G__E__P__K__D__P__V__Q__V__P__K__L__L__I__

121  CGTGGTGGTGTCGAGGTGCTGGAAGTCAAGACCGGCGTGGACTCCATTACCGAGGTGGAG
      R__G__G__V__E__V__L__E__V__K__T__G__V__D__S__I__T__E__V__E__

181  TGCTTCCTCACCCCCGAGATGGGTGACCCTGACGAGCACCTGAGGGGCTTCTCCAAGTCC
      C__F__L__T__P__E__M__G__D__P__D__E__H__L__R__G__F__S__K__S__

241  ATCTCCATCTCCGACACCTTCGAGTCCGACTCCCCCAACCGTGACATGCTGCCCTGCTAC
      I__S__I__S__D__T__F__E__S__D__S__P__N__R__D__M__L__P__C__Y__

301  TCCGTGGCTCGTATCCCCCTGCCCAACCTGAACGAGGACCTGACTTGCGGCAACATCCTG
      S__V__A__R__I__P__L__P__N__L__N__E__D__L__T__C__G__N__I__L__

361  ATGTGGGAGGCTGTGACCCTCAAGACCGAGGTCATCGGCGTGACTTCCCTGATGAACGTG
      M__W__E__A__V__T__L__K__T__E__V__I__G__V__T__S__L__M__N__V__

421  CACTCCAACGGCCAGGCTACCCACGACAACGGTGCTGGCAAGCCCGTGCAGGGAACCTCC
      H__S__N__G__Q__A__T__H__D__N__G__A__G__K__P__V__Q__G__T__S__

481  TTCCACTTCTTCTCCGTGGGTGGCGAGGCTCTGGAACTCCAGGGCGTGGTGTTCAACTAC
      F__H__F__F__S__V__G__G__E__A__L__E__L__Q__G__V__V__F__N__Y__

541  CGTACCAAGTACCCCGACGGCACCATCTTCCCCAAGAACGCTACTGTGCAGTCCCAAGTG
      R__T__K__Y__P__D__G__T__I__F__P__K__N__A__T__V__Q__S__Q__V__

601  ATGAACACCGAGCACAAGGCTTACCTGGACAAGAACAAGGCCTACCCCGTGGAGTGCTGG
      M__N__T__E__H__K__A__Y__L__D__K__N__K__A__Y__P__V__E__C__W__

661  GTGCCCGACCCCACCCGTAACGAGAACACCCGTTACTTCGGCACCCTGACCGGTGGAGAG
      V__P__D__P__T__R__N__E__N__T__R__Y__F__G__T__L__T__G__G__E__

721  AACGTGCCCCCCGTGCTGCACATCACCAACACCGCTACCACCGTGCTGCTGGACGAGTTC
      N__V__P__P__V__L__H__I__T__N__T__A__T__T__V__L__L__D__E__F__

781  GGTGTCGGTCCCCTGTGCAAGGGCGACAACCTGTACCTGTCCGCTGTGGACGTGTGCGGC
      G__V__G__P__L__C__K__G__D__N__L__Y__L__S__A__V__D__V__C__G__

841  ATGTTCACCAACCGTTCCGGTTCCCAGCAGTGGCGTGGCCTGTCCCGCTACTTCAAGGTG
      M__F__T__N__R__S__G__S__Q__Q__W__R__G__L__S__R__Y__F__K__V__

901  CAGCTGCGCAAGCGTCGTGTGAAGAACCCCTACCCTATCTCCTTCCTGCTGACCGACCTG
      Q__L__R__K__R__R__V__K__N__P__Y__P__I__S__F__L__L__T__D__L__

961  ATCAACCGTCGTACCCCTCGTGTGGACGGCCAGCCCATGTACGGCATGGACGCTCAGGTG
      I__N__R__R__T__P__R__V__D__G__Q__P__M__Y__G__M__D__A__Q__V__

1021  GAAGAGGTCCGCGTGTTCGAGGGCACCGAGGAATTGCCCGGCGACCCCGACATGATGCGT
      E__E__V__R__V__F__E__G__T__E__E__L__P__G__D__P__D__M__M__R__

1081  TACGTGGACAAGTACGGCCAGCTCCAGACCAAGATGCTGTAACTGCAGTCTCGAGGCATG
      Y__V__D__K__Y__G__Q__L__Q__T__K__M__L__*__
```

METHOD FOR PURIFYING VIRUS-LIKE PARTICLES (VLP)

CROSS REFERENCE TO PRIOR APPLICATIONS

This application is a U.S. National Phase application under 35 U.S.C. §371 of International Application No. PCT/EP2012/003273, filed on Aug. 1, 2012 and which claims benefit to European Patent Application No. 11176295.1, filed on Aug. 2, 2011. The International Application was published in German on Feb. 7, 2013 as WO 2013/017272 A1 under PCT Article 21(2).

FIELD

The present invention relates to a method for purifying VLP-containing compositions and to high-purity VLP-containing compositions and also to the use thereof in diagnostic or therapeutic methods.

BACKGROUND

In the development of specific diagnostic or therapeutic methods, the use of transfer systems (delivery systems) are of great importance which permit a transfer as cell-specific as possible of substances such as nucleic acid, markers or active ingredients. For this cell-specific transfer, inter alia, a system based on virus-like particles (VLP) has been developed (WO 97/19174; EP 1 270 586 B1). The basis of this system is the property of the VLP to be able, for example, to package active ingredients or nucleic acids, and then to implant them specifically into defined cells.

VLPs can be produced, for example, by recombinant expression of the main structural protein VP1 of the human polyomavirus JCV (VP1-VLPs). In contrast to VP1 expression of other polyomaviruses, the VP1-VLPs are secreted into the supernatant of the host cell cultures. For purification of the VP1-VLPs from the cell culture supernatant, a plurality of methods have already been developed. However, these are not all suitable for producing VLPs on a commercial scale (large scale). This is true in particular when the production process must be GMP-certifiable, since particularly high demands are then made on the purity of the VLPs.

For instance, Goldmann et al. (J. Virol., 1999, 73: 4465-4469) describe the purification of VP1-VLPs expressed in insect cells by density centrifugation using a 40% strength sucrose solution followed by a density centrifugation using 40% sucrose and 50% metrizamide(2-({3-(acetylamino)-5-[acetyl(methyl)amino]-2,4,6-triiodobenzoyl}amino)-2-deoxy-D-glucopyranose. This method is unsuitable not only for large scale production. Also, the VP1 proteins provided in this way are contaminated with VP1 fragments of 38 and 40 kDa.

For purification of recombinant VLPs from lysed *E. coli* cells, Pushko et al. (Protein Engineering, 1993, 6(8): 883-891) use an ammonium sulfate precipitation with subsequent gel permeation chromatography with the use of a Sephadex G25 column and a G100 column.

WO 92/13081 A1 discloses a purification method for isolating VLPs derived from MS-2 by fractional ammonium sulfate precipitation and subsequent isoelectric point precipitation, sucrose density centrifugation and gel permeation chromatography.

WO 2006/136566 A9 describes the purification of recombinant bacterially expressed VLPs via an anion-exchange chromatography followed by a hydroxyl apatite column and an optional gel permeation chromatography.

The methods known from this prior art are insufficiently suitable for preparing the VLPs outside a laboratory scale since they are either very complex, do not permit upscaling to an industrial method and/or do not meet the high requirements of a GMP-conforming process. The latter especially applies due to contaminants, which, inter alia, can also be enclosed in the VLPs.

SUMMARY

Therefore, the object of the invention is to provide a production method for VLPs which reduces at least one a disadvantage of the known production methods or even substantially avoids it.

This object is achieved according to the invention by the method of the main claim. Advantageous embodiments are subject matter of corresponding subclaims. In addition, VLP compositions of a defined purity are claimed, just as are advantageous VP1 proteins.

BRIEF DESCRIPTION OF THE DRAWINGS

The present invention is described in greater detail below on the basis of embodiments and of the drawings in which:

FIG. 1 shows a flow diagram for producing VP1-encoding baculoviruses by transfection of SF9 insect cells;

FIG. 5: shows a flow diagram for the VLP production method: Part 3a—Dissociation of the VLPs and purification of the pentamers by means of a weak anion exchanger;

FIG. 6: shows a flow diagram for the VLP production method: Part 3b—Purification of the VLPs by dissociation and chromatography using a strong anion exchanger; and FIG. 7: Amino acid sequence of the VP1 capsid protein derived from the polyoma virus JC (SEQ ID NO: 3) in addition to the nucleotide sequence encoding for the same (SEQ ID NO: 16), which was codon-optimized for expression in insect cells.

DETAILED DESCRIPTION

Figure 2:
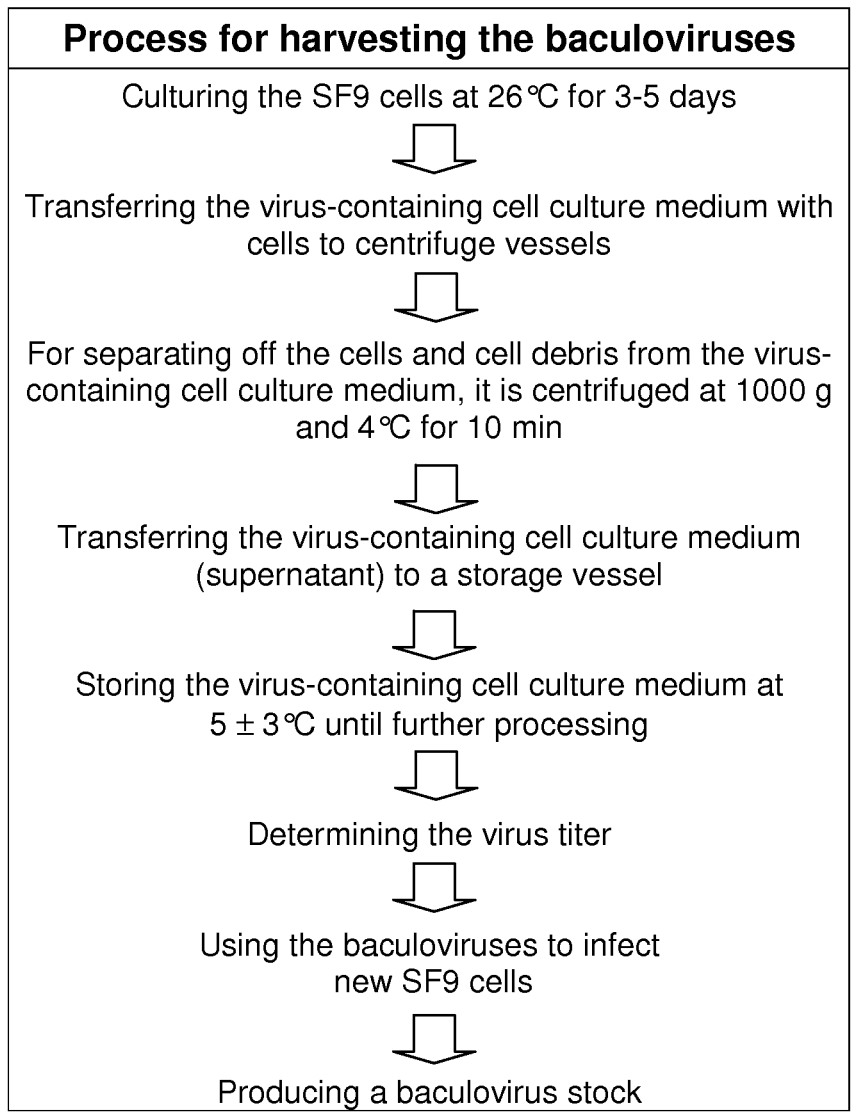
FIG. 2: shows a flow diagram for harvesting the baculoviruses for establishing a "seed strain"
Figure 3:
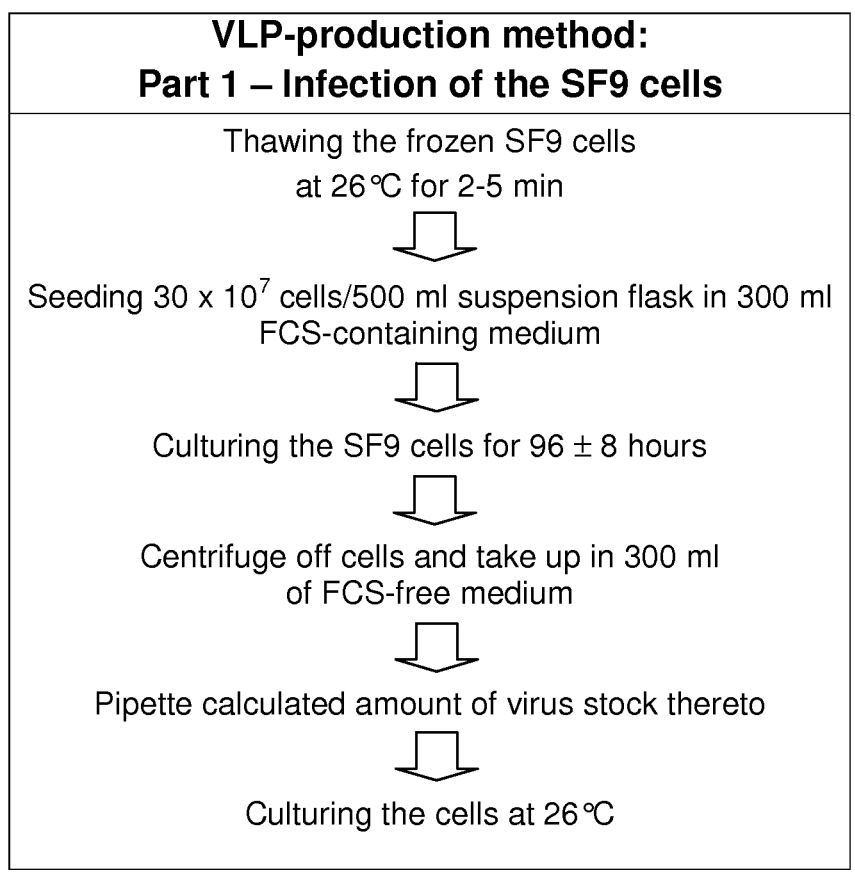
FIG. 3: shows a flow diagram for the VLP production method: Part 1—Infection of the SF9 cells.
Figure 4:
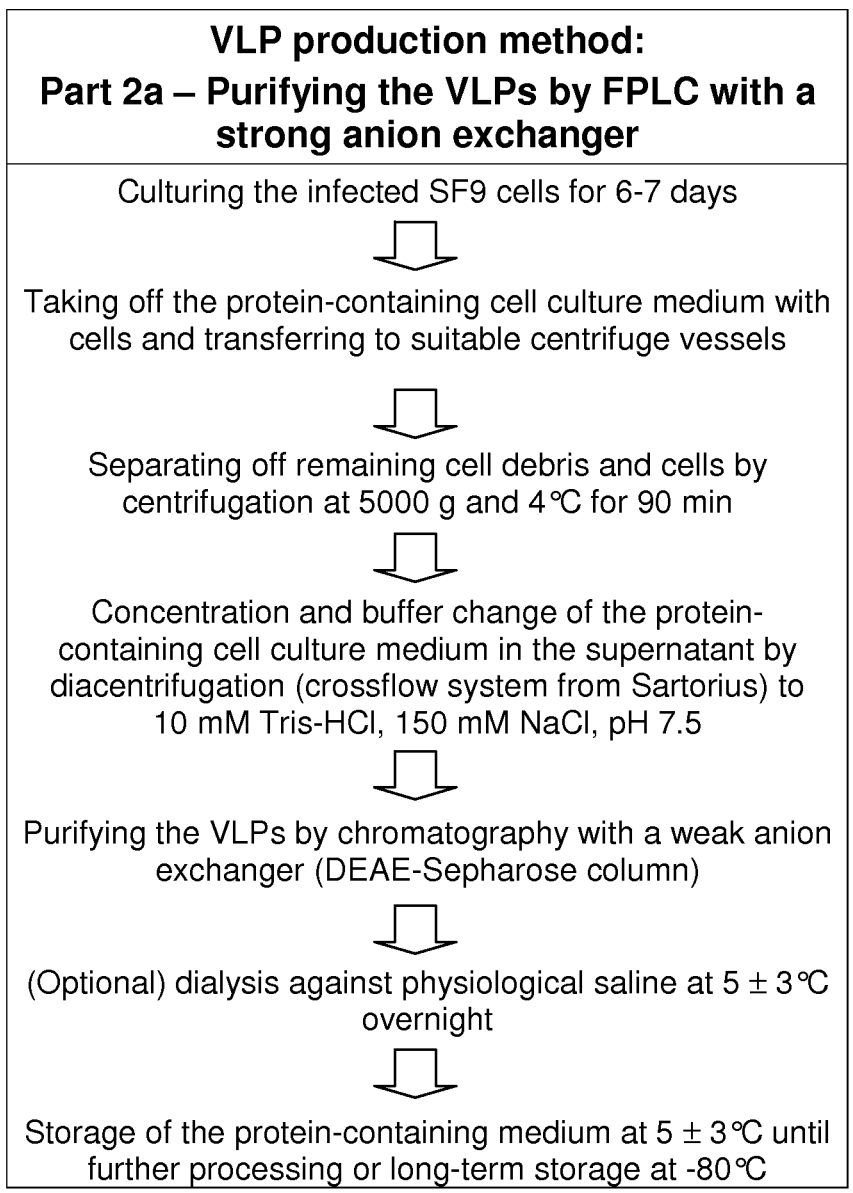
FIG. 4: shows a flow diagram for the VLP production method: Part IIa—Purification of the VLPs by FPLC with a strong anion exchanger.

The present invention provides a method for effective purification of VLPs. The method has the particular advantage that large scale production is permitted which also satisfies the high requirements of a good manufacturing practice (GMP) process.

The method according to the invention for purifying VLPs is distinguished in that a VLP-containing composition is filtered through a filter medium, in particular a membrane, wherein the filter medium has an exclusion limit (molecular weight cut-off (MWCO)) of more than 30 kDa and the VLP-containing composition used is the cell culture supernatant of VLP-expressing cells. The inventors have established that using such a step at the start of a downstream process—which in the prior art is carried out if at all after at least one chromatography step—simple and efficient purification of the VLPs is possible.

In the filtration of the VLPs by the filter medium used according to the invention, possible contaminants pass through the filter medium and arise in the filtrate, while the high-molecular-weight VLPs remain in purified form in the retentate. This single-stage method first permits simple separation of the VLPs from the contaminants present in the composition.

Depending on regulation of the method, in this purification step, a concentration of the VLP-containing composition can be achieved, since during the filtration, of course, the liquid volume of the retentate decreases and the relative proportion of VLPs in the retentate increases. A concentration is advantageous in many purification methods, because subsequent steps such as a column-chromatographic purification, for example, may be carried out more efficiently and inexpensively thereby.

In addition, this purification step can be used to modify the solution conditions of the VLP-containing composition by, e.g., exchanging the buffer (buffer exchange). This operation is also termed diafiltration.

The purification method in addition has at least one of the following advantages:

It is a gentle purification method which leaves the VLPs as far as possible in their native form, which is essential for their activity. In the case of methods of the prior art, in contrast, modifications of the VLP surface (e.g. with respect to charge changes) sometimes occur, which can have disadvantageous effects on the subsequent use or processing of the VLPs.

The use of organic solvents can be avoided, which otherwise can be associated with the risk of protein denaturation.

The ionic environment and the pH of the VLP-containing composition can be retained if required.

The filtration step according to the invention is rapid and inexpensive. In addition, it is efficient and can be used simultaneously for purification, concentration and/or buffer exchange.

It can be carried out at low temperatures, for instance in a cold room, for example.

The particular advantage of the method according to the invention, however, is that, via only one step, a considerable improvement of the purity of the VLPs is achievable in a vey highly complex and highly contaminated composition. This also applies to complex compositions such as a cell culture supernatant. The purity of the VLP-containing composition after the filtration according to the invention can thus be at least 70%, advantageously at least 75%, or at least 80%. The purity can be further increased by further purification processes.

Definitions

The expressions used in the description and the claims, where they are not otherwise specified, have the meaning defined hereinafter:

The expression "virus-like particle (VLP)" for the purposes of the invention relates to a particulate structure in which a plurality of proteins are present in aggregated form, wherein they preferably enclose a cavity. At least a part of the structure-forming proteins is identical to, or derived from, viral structural proteins (capsid proteins), in particular from viruses of the Papoviridae family. This comprises the family of the Papillomaviridae and also the family of the Polyomaviridae. The VLPs, however, can also originate from other virus families such as, e.g., the Parvoviridae, Flavoviridae and Retroviridae families.

Preferably, a VLP is formed by 60, 72, 120, 180, 240, 300, 360 and more than 360 viral structural proteins and can have a tubular or spherical structure. A VLP made of 360 structural proteins is usually made up of 72 pentamers which are each formed by five monomeric structural proteins. The aggregation of the structural proteins and pentamers can proceed via non-covalent or covalent bonding of the proteins. In the case of a covalent bonding, a formation of disulfide bridges is preferred.

A VLP can be composed either of a multiplicity of only one structural protein, or else of different structural proteins. Preference is given to the presence of only one structural protein, namely VP1, or of L1 (see hereinafter).

The structural proteins of the VLPs, in particular VP1 (or else VP2 and/or VP3) can be identical to or derived from the structural proteins, e.g. of the following viruses from the Polyomaviridae family: African green monkey polyomavirus (AGMPyV), pavian polyomavirus 2 (BPyV-2), human polyomavirus 1 (BK virus, BKV or BKPyV), human polyomavirus 2 (JC virus, JCV or JCPyV), bovine polyomavirus (BPyV), budgerigar polyomavirus (polyomavirus of budgerigar fledging disease, BFPyV), hamster polyomavirus (HaPyV), murine pneumotropic virus (MPtV), murine polyomavirus (MPyV), rabbit polyomavirus (rabbit kidney vacuolating virus, RKV), simian virus 12 (SV-12), simian virus 40 (SV-40), crow polyomavirus, goose hemorrhagic polyomavirus (GHPV), merkel cell polyomavirus, chimpanzee polyomavirus, finch polyomavirus and KI polyomavirus (KIV).

However, the VLPs can also correspond to the structural proteins of the viruses, preferably the L1 (but also L2) of the Papillomaviridae family, or are derived therefrom, namely, for example, from the following virus genera: Alphapapillomavirus, Betapapillomavirus, Gam mapapillomavirus, Deltapapillomavirus, Epsilonpapillomavirus, Zetapapillomavirus, Etapapillomavirus, Thetapapillomavirus, Iotapapillomavirus, Kappapapillomavirus, Lam bdapapillomavirus, Mupapillomavirus, Nupapillomavirus, Xipapillomavirus, Om ikronpapillomavirus, Pipapillomavirus, Trichosurus-vulpecula-Papillomavirus, and Opossum-Papillomavirus.

The VLP according to the invention can, in addition, have one or more additional heterologous proteins in the capsid, i.e. proteins which are not identical or similar to a protein of a virus of the Papoviridae family. Suitable heterologous protein are in principle all proteins which can be incorporated into the capsid, or bind to the capsid, and do not significantly impair the assembly of the VLP.

A "VLP-containing composition", is any composition which contains VLPs, preferably a liquid. In this case the expression "liquid", in delimitation from a solid, comprises all free-flowing compositions, that is to say also high-viscosity, oily or else bituminous liquids. The composition can be single-phase or multiphase. The VLPs can be present in dissolved form, but also possibly, with aggregate formation, as dispersed or suspended particles.

According to the invention, the expression "filter medium" relates to any filter medium which permits solid/liquid separation. Preferably, it is present as a porous matrix which separates at least two compartments and permits the passage of individual substances from one compartment into at least one second compartment. Such a method which is carried out using a filter medium is, in the context of the present invention, to be understood as "filtration".

A "membrane", for the purposes of the invention, is a usually planar extended structure which has pores. Preferably, the membrane is flexible and consists of a polymer or polymer mixture. As polymer, according to the invention, in particular polyethersulfone or cellulose (in particular regenerated cellulose) are used.

According to the invention, the "exclusion limit" (also "separation limit") indicates the retention rate of the filtration. It is usually related to the molar mass and reported in Dalton (Nominal Molecular Weight Cut-Off NMWC, also MWCO, Molecular Weight Cut-Off). It is defined as the minimum molecular mass of a molecule which is retained by the filter medium.

A "pentamer" in the context of the invention is a structure which is formed by five polypeptide subunits. The bonding between the individual polypeptide subunits can proceed via noncovalent or covalent bonding. The five subunits frequently form a ring-shaped structure having pentagonal symmetry. Here, generally, each subunit interacts with two adjacent subunits in each case.

"Dissociation", in the context of the invention, is taken to mean the process in which the integrity of the VLP is impaired in such a manner that space which is preferentially enclosed by the VLP becomes connected to the outer medium surrounding the VLP and/or capsid proteins are separated off from the VLP. Typically, this is achieved by the cleavage of some polypeptides or proteins which form the VLP. In this case, the VLP can also disintegrate entirely into its subunits, such as, e.g., VP1 or L1 pentamers.

According to the invention, a "reassociation" is a partial or complete restoration of a VLP starting from a preceding VLP dissociation.

The abbreviation "GMP" is short for "Good Manufacturing Practice Regulations". The rules and measures recognized for the production of medicaments and foods are compiled in these basic rules of the World Health Organization which, on the basis of the current prior art, guarantee safe production for the costumers (patients or consumers). The GMP rules demand, in addition to an appropriate infrastructure of personnel, rooms and machinery, a system of safety measures which extends over the entire production process from input control to output control.

"Contaminants" are taken to mean those components of the VLP-containing composition which are undesirable in the composition and should therefore be depleted as far as possible. These can be, e.g., salts, low-molecular weight or else macromolecular compounds. The elimination of the contaminants by purification leads to an increase in the purity of the desired substance, that is to say to the increase in the quantitative fraction of the desired substance (here VLPs) of the entire mixture of matter.

The expressions "anion exchanger" or "anion exchange matrix" are synonymous and both refer to natural or artificial substances which can bind anions and can exchange these for anions from a surrounding medium. An anion exchanger carries positive ions and exchanges negatively charged counterions.

"Strong anion exchangers" for the purposes of the invention carry quaternary ammonium groups of type I:

or of type II:

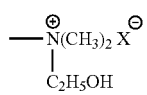

where X is an anion,
which is selected from the group consisting of hydroxyl, chloride, sulfate, bromide, iodide, fluoride, sulfide, hydrogensulfate, hydrogensulfide, phosphate, diphosphate, monophosphate, carbonate, hydrogencarbonate, citrate, tartrate and phthalate. A commercially available column having a strong anion exchange matrix is, for example, the Mono Q column from GE Healthcare (Munich, Germany).

"Weak anion exchangers", for the purpose of the invention, carry tertiary or secondary amine groups as functional groups, such as diethylaminoethyl (DEAE) groups, for example. A commercially available weak DEAE anion exchange matrix is, for example, the "Sartobind Q membrane adsorber" from Sartorius (Gottingen, Germany).

The expression "ultrafiltration" relates to a method in which a liquid is brought into contact (typically under pressure) with a filter medium, in particular a semipermeable membrane. The pressure can be applied by exerting a pressure onto the liquid situated above the filter membrane or by centrifugation of the filter unit. Alternatively, by applying a negative pressure below the filter membrane, the passage of the solution can be accelerated. The membrane contains pores of a defined size, in such a manner that molecules or complexes which are small enough in order to be able to pass through the pores migrate through the membrane to the opposite side, whereas molecules or complexes which are too large in order to be able to pass through the pores remain on the application side of the membrane. Ultrafiltration membranes typically consist of polymers or polymer mixtures and are designed for a specific molecular weight separation limit (exclusion limit).

The expression "diafiltration" relates to a form of ultrafiltration which combines the properties of the dialysis with those of ultrafiltration. The addition of a solvent to the retentate of the filtration permits a change or dilution of the original solvent (e.g. "buffer exchange").

A "cell culture supernatant", in the context of the invention, is the cell-culture-derived part of the cell culture which is essentially free from VLP-secreting cells. In a preferred embodiment of the invention, the cell culture supernatant contains less than 5%, preferably less than 2%, in particular less than 1%, VLP-secreting cells. The cell culture supernatant customarily contains a high fraction of contaminants (e.g. cell debris, proteins or fragments thereof). The cell culture supernatant can be treated, e.g. chemically or physically. The supernatant can also be centrifuged. However, it can also be purified according to the invention untreated, i.e. without centrifugation, for example. Preferably, it is centrifuged, but not chemically or enzymatically treated. The expression cell culture supernatant assumes according to the invention that a chromatography of the harvested starting medium has not taken place.

"Chromatography" denotes a method which permits the separation of a mixture of substances by differing distribution of the individual components thereof between a stationary phase and a mobile phase. Centrifugation in this sense is not chromatography.

"Reversed phase" chromatography denotes a method in which the stationary phase is a nonpolar phase and the mobile phase is a polar phase. Any inert nonpolar substance which may also be packed as a column can be used for "reversed phase" chromatography. Examples of stationary phases are a silica-bound octadecyl radical (C18), octyl radical (C8), a silica material carrying Cyano groups or phenyl groups, or pure silica material. As a nonpolar phase. In HPLC in this case frequently a gradient elution is employed, wherein the composition of the solvent is slowly modified (e.g. from 80% to 20% water fraction). In this manner nonpolar components emerge very late from the column and polar components very early from the column and they may be separated from one another thereby.

A "cell lysate", in the context of the invention, is a composition which results from the lysis of cells. Lysis, as destruction of cellular integrity, can be achieved by chemical methods (e.g. detergents), biological methods (e.g. enzymatic treatment) and/or physical methods (e.g. ultrasonic treatment, shear forces). In this context, a cell lysate can be a cell culture supernatant.

The expression "cell-free in vitro translation mixture" relates to an experimental method in molecular biology, by means of which mRNA molecules isolated from cells or generated by means of in-vitro transcription are used in the reaction vessel for protein biosynthesis (translation). In this case, so called in-vitro translation systems are helpful which contain the necessary enzymes and tRNA molecules and also amino acids, so that, after addition of the mRNA, protein synthesis occurs. Frequently, methionine labeled with the sulfur isotope $^{35}S$ is added to the reaction mixture in order to be able to detect the translation products. Common cell-free systems are wheat germ extract and reticulocyte lysate.

THE INVENTION IN DETAIL

According to the invention, a VLP-containing composition is filtered through a filter medium having an exclusion limit of greater than 30 kDa. It can be preferable to use a filter medium having an exclusion limit of at least 40 kDa. In a particular embodiment, the exclusion limit of the filter medium is 80 to 1500 kDa; particular preference is given to an exclusion limit of about 100 kDa.

A filter medium which has an exclusion limit in the abovementioned range also permits the efficient separation of higher-molecular-weight contaminants from the VLP-containing composition, minimizing the loss of yield of VLPs.

The VLP-containing composition is the cell culture supernatant from the cell culture of VLP-secreting cells. This cell culture supernatant can be taken off directly from the cell culture and then be filtered according to the invention. In one embodiment of the invention, however, it is also possible that the cell culture supernatant is treated in advance, e.g. chemically, enzymatically or thermally. This treatment can in some circumstances facilitate the filtration according to the invention, without leading away from the invention itself.

The filter medium usable according to the invention can consist of a polymer or a polymer mixture. Preference is given in this case to a polymer or polymer mixture selected from the group comprising cellulose, polyethersulfone (PES), cellulose triacetate (CTA), cellulose acetate, cellulose nitrate, polyacrylnitrile (PAN) polyamide, polycarbonate and polytetrafluoroethylene (PTFE). These polymers form stable filter membranes which are inert, do not have a tendency to protein aggregation and can be provided with cavities of a controlled diameter.

In one embodiment of the invention, during the filtration, between the filtrate-side and retentate-side compartments, a pressure difference between 0.5 bar and 10 bar, preferably between 0.5 and 5 bar, and particularly preferably between 0.5 bar and 3 bar, is built up.

Numerous methods are available to a person skilled in the art in order to build up and regulate a corresponding pressure. For instance, by centrifugation of the filter unit a pressure forming in accordance with the centrifugal acceleration g is exerted on the retentate. In addition, by applying a retentate-side overpressure, e.g. by means of a pump, or a punch, a pressure can be built up. Alternatively, the pressure difference can be built up by applying a filtrate-side negative pressure, e.g. via a vacuum pump. The pressure difference can be kept constant over the purification time, but a pressure difference varying with time can alternatively be built up, which, as a filtration program, for example, contains differing phases having separate time period and differing pressure.

In a preferred embodiment, the filtration can be carried out as what is known as "cross-flow filtration" (also termed "tangential flow filtration"). In this case, a cross-flow having a high velocity of, e.g., about 2.5 to 3 m/s can be generated which flows along a membrane or a filter medium. The high velocity avoids a filtercake (covering layer or fouling) of the solids particles to be separated off being able to build up on the membrane.

In an alternative embodiment of the invention, the filtration can also be carried out in the dead-end method, however. In dead-end filtration, a feed stream, in order to minimize compacting of the retained substances, is pumped against the membrane with the lowest possible pressure. Due to the permanent drainage of the permeate, a filtercake (covering layer or fouling) or a concentration gradient (concentration polarization) of the protein particles to be separated off accumulates on the membrane. The filtercake increases the filtration resistance and thereby the pressure drop across the membrane. The filtercake must be removed at regular intervals, depending on feed composition, by backwashing (reverse pumping of medium that has already been separated) and chemical cleaning, and the filter element thereby be regenerated.

According to the invention, the filter medium can have various geometries, thus, e.g., it can be constructed as a helically coiled membrane, tubular membrane or hollow fiber membrane. The differing filter geometry takes into account the process conditions with respect to solution volume, concentration/amount of VLPs or contaminants, or applied pressure difference.

In the case of the purification method according to the invention, in addition to the abovementioned cell culture supernatant, other VLP-containing compositions can also be used. Possible media according to the invention are therefore selected from the group of the following media:
(a) cell culture supernatant from culturing VLP-expressing cells;
(b) cell culture supernatant according to (a) after purification via centrifugation and/or dialysis;
(c) cell lysate of (a);
(d) cell lysate (according to (a)) after purification via centrifugation and/or dialysis;
(e) cell-free in vitro translation mixture; or
(f) cell-free in vitro translation mixture after purification via centrifugation and/or dialysis.

In a further embodiment of the invention, in addition to the purification, a concentration of the VLP-containing composition is also achieved. This is preferably performed in that the retentate volume that decreases during the filtration is not replenished, or is only partially replenished.

In an additional embodiment of the invention, in addition to the purification, a buffer exchange of the VLP-containing composition is also achieved. This buffer replacement is preferably performed in that the retentate volume decreasing during the filtration is replaced by a buffer having a composition differing with respect to the starting buffer.

In this case, in a preferred embodiment, the pH is reduced, wherein a pH close to the pI of the capsid proteins is advantageous. In the case of the VLPs consisting of VP1, this is a pH between 5.0 and 8.0. This lowered pH results in a reduced stability of the VLPs which can therefore be more readily dissociated in a subsequent dissociation step, and thus, for example, smaller amounts of disulfide bond-cleaving reducing agent and $Ca^{2+}$ ion-binding complexing agent need to be used.

In an embodiment of the invention, the VLP-containing composition purified by the method according to the invention is additionally purified chromatographically, preferably via anion-exchange chromatography.

Preferably, the additional purification is performed by fractionation using a (in particular weak) anion exchanger. This contains, as functional groups, primary, secondary or tertiary amine groups, wherein diethylaminoethyl (DEAE) groups are preferred. In a preferred embodiment of the invention, the matrix of this anion exchanger consists of DEAE-Sepharose.

The VLPs or VP1 pentamers can be eluted from this anion exchanger according to the invention by an NaCl-containing solution, which preferably contains NaCl in a concentration of 150 mM to 750 mM, particularly preferably 300 mM NaCl.

In a further embodiment of the invention, the additional purification of the VLPs by means of an anion exchanger comprises the following steps:
(a) providing the VLP-containing composition purified by means of ultrafiltration;
(b) contacting the VLP-containing composition with an anion exchanger under conditions which permit binding of the VLPs to the anion exchanger;
(c) optional washing of the anion exchanger;
(d) elution of the bound VLPs;
(e) optional dialysis of the VLPs against an aqueous solution.

Preferably, for this purpose, a weak anion exchanger is used.

In a further embodiment of the invention, the VLP-containing composition purified according to the invention is in this case purified with a strong anion exchanger which contains quaternary ammonium groups of type I or type II:

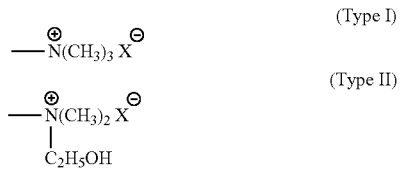

wherein X is an anion selected from the group consisting of hydroxyl, chloride, sulfate, bromide, iodide, fluoride, sulfide, hydrogensulfate, hydrogensulfide, phosphate, diphosphate, monophosphate, carbonate, hydrogencarbonate, citrate, tartrate or phthalate.

In a preferred aspect of the invention, in this case, the strong anion exchanger used is a Q-Sepharose matrix or a MonoQ column.

The VLPs can be eluted from the strong anion exchanger by one or more NaCl-containing aqueous solutions. In this case, the NaCl concentration can be varied by a linearly increasing gradient, or by a stepwise gradient.

As linear NaCl gradient, a gradient is preferred in which the NaCl concentration of the elution buffer increases from initially 100 mM to 1 M NaCl. As NaCl stepwise gradient, a three-step or a four-step gradient is preferred.

The three-step NaCl stepwise gradient can preferably consist of the following steps:
(i) 50 mM to 150 mM NaCl,
(ii) 200 mM to 400 mM NaCl,
(iii) 1 M to 2 M NaCl; or the four-step NaCl stepwise gradient can preferably consist of the following steps:
(i) 50 mM to 150 mM NaCl,
(ii) 200 mM to 400 mM NaCl,
(iii) 500 mM to 800 mM NaCl,
(iv) 1 M to 2 M NaCl.

In a further embodiment of the invention, the VLP-containing composition purified by the inventive method is additionally purified by means of gel filtration or by means of ceramic hydroxyapatite column chromatography. These methods permit separation of the VLPs from capsid monomers or capsid oligomers, such as pentamers for example.

In an embodiment of the invention, the VLPs purified by the method according to the invention are purified by a method according to the following steps:
(a) dissociation of the VLPs;
(b) purifying the dissociated VLPs;
(c) reassociation of the dissociated VLPs.

The dissociation of the VLPs preferably proceeds in the presence of a disulfide-bond-cleaving reducing agent and a $Ca^{2+}$-ion-binding complexing agent.

In one aspect of the invention, as disulfide-bond-cleaving reducing agents, sulfur compounds are used, preferably selected from the group consisting of 2-mercaptoethanol (2-ME), dithiothreitol (DTT), dithioerythrol (DTE), glutathione, tris(2-carboxyethyl)phosphine (TCEP), monothioglycerol, and particularly preferably DTT.

In cases where toxicity is particularly critical, disulfide-bond-cleaving reducing agents to be preferred are 2-mercaptoethanol (2-ME) and monothioglycerol. 2-ME can be simply removed on account of its volatility, monothioglycerol, in contrast, is also suitable for subsequent use in cell culture.

The sulfur-containing reducing agents are weak reducing agents, the redox potential of which is sufficient, however, in order to reduce the disulfide bonds to the free cysteine residues. The use of such weak reducing agents has the advantage that other functional groups of the VLPs are not reduced, and thus the integrity and native properties of the VLPs are substantially retained. According to the invention, other reducing agents can also be used, the redox potential of which is in the range of the abovementioned sulfur-containing reducing agents.

In a further aspect of the invention, the complexing agent binding the $Ca^{2+}$-ions used in the dissociation is a chelating agent, preferably selected from the group consisting of citric acid, ethylenediaminetetraacetic acid (EDTA), ethylene glycol tetraacetic acid (EGTA) or the corresponding salts of these acids, and particularly preferably EGTA.

In one embodiment of the invention, the dissociated VLPs which are preferably present as capsid proteins—particularly preferably as VP1 or L1 proteins—are additionally purified chromatographically, preferably via anion-exchange chromatography, or reverse phase chromatography.

In a preferred embodiment, in this case, a strong anion exchanger is used which contains quaternary ammonium groups of type I or type II:

-continued

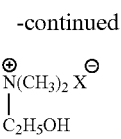
(Type II)

wherein X is an anion selected from the group consisting of hydroxyl, chloride, sulfate, bromide, iodide, fluoride, sulfide, hydrogensulfate, hydrogensulfide, phosphate, diphosphate, monophosphate, carbonate, hydrogencarbonate, citrate, tartrate or phthalate.

In one preferred aspect of the invention, in this case, the strong anion exchanger used is a Q-Sepharose matrix or a MonoQ column.

The dissociated VLPs (or the structural proteins thereof) can be eluted from the strong anion exchanger according to the invention by one or more NaCl-containing aqueous solutions. Here, the NaCl concentration can be varied by a linearly increasing gradient, or a stepwise gradient.

As linear NaCl gradient, a gradient is preferred in which the NaCl concentration of the elution buffer increases from initially 100 mM to 1 M NaCl. As NaCl stepwise gradient, a three-step or a four-step gradient is preferred.

The three-step NaCl stepwise gradient can preferably consist of the following steps:
  (i) 50 mM to 150 mM NaCl,
  (ii) 200 mM to 400 mM NaCl,
  (iii) 1 M to 2 M NaCl; or
the four-step NaCl stepwise gradient can preferably consist of the following steps:
  (i) 50 mM to 150 mM NaCl,
  (ii) 200 mM to 400 mM NaCl,
  (iii) 500 mM to 800 mM NaCl,
  (iv) 1 M to 2 M NaCl.

In a further embodiment of the invention, the purification of the dissociated VLPs by means of an anion exchanger comprises the following steps:
  (c) contacting the dissociated VLP-containing composition with an anion exchanger under conditions which permit binding of the dissociated VLPs to the anion exchanger;
  (d) optional washing of the anion exchanger;
  (e) elution of the bound dissociated VLPs;
  (f) optional dialysis of the dissociated VLPs against an aqueous solution.

Preferably, for this purpose, a strong anion exchanger is used.

The dissociated VLPs can also be purified according to the invention by a weak anion exchanger. This contains as functional groups primary, secondary or tertiary amine groups, wherein diethylaminoethyl (DEAE) groups are preferred. In a preferred embodiment of the invention, the matrix of the weak anion exchanger consists of DEAE-Sepharose.

The dissociated VLPs are eluted according to the invention from the weak anion exchanger by an NaCl-containing solution, which preferably contains NaCl in a concentration of 150 mM to 750 mM, particularly preferably 300 mM.

In a further embodiment of the invention, the purification of the dissociated VLPs by means of an anion exchanger comprises the following steps:
  (c) contacting the dissociated VLP-containing composition with an anion exchanger under conditions which permit binding of the dissociated VLPs to the anion exchanger;
  (d) optional washing of the anion exchanger;
  (e) elution of the bound dissociated VLPs;
  (f) optional dialysis of the dissociated VLPs against an aqueous solution.

Preferably, for this purpose, a weak anion exchanger is used.

In an embodiment of the invention, the dissociated VLPs are purified via reverse phase chromatography. Preferably, here, purification is via high-performance liquid chromatography (HPLC) using a reverse phase column. It permits in a short time purification even of large amounts of dissociated VLPs.

In a further embodiment of the invention, the dissociated VLPs are purified via gel permeation chromatography. This method is preferably used in those cases in which modified capsid proteins, owing to the modification (in particular insertions or deletions), have a different molecular weight and therefore may be separated from the unmodified capsid proteins.

The dissociated VLPs can optionally be purified by an additional dialysis, in order to carry out, e.g., an exchange of the buffer components. Preferably, for the dialysis, a buffer is used which is osmomolar with respect to the blood. Particular preference in this case is given to the use of physiological saline as a dialysis buffer.

The dialysis is preferably carried out at a temperature below room temperature, wherein a temperature of 5±3° C. is preferred. The duration of the dialysis is expediently at least 12 hours and is preferably longer than 16 hours. The dialysis can last up to 48 hours.

For storage of the dissociated VLPs, it is advantageous to take up the dissociated VLPs in a buffer having a low pH (5.0 to 7.5) and having an elevated NaCl concentration (250 mM to 500 mM). As a result, aggregation is prevented. Storage then proceeds at a temperature of −80° C. Alternatively, the dissociated VLPs can also be converted into a stable storage form by lyophilization.

In a particular embodiment, the VLPs can contain one or more substances in the interior of the capsid structure. Such substances comprise, e.g., macromolecules such as nucleic acids, i.e. RNA, DNA, or artificially modified nucleic acids, and proteins and other physiologically active substances which can be of natural, synthetic or recombinant type. Examples of such physiologically active substances are, e.g., lipids, phospholipids, peptides, medicaments, toxins etc.

Reassociation of the purified VLPs which are optionally loaded with active ingredient can proceed by dialysis with a reassociation buffer which contains divalent cations, or else the monovalent cation $Rb^+$. This buffer preferably contains a cation selected from the group consisting of $Mg^{2+}$, $Rb^+$ or $Zn^{2+}$, and particularly preferably $Ca^{2+}$. The reassociation buffer contains 0.1 mM to 10 mM $Ca^{2+}$ ions, preferably 0.5 mM to 5 mM $Ca^{2+}$ ions and especially 1 mM $CaCl_2$.

In a further embodiment of the invention, the VLPs loaded with the active ingredient are purified by gel permeation chromatography. This permits separation of the active ingredient molecules from the VLPs loaded with the target molecules.

In a further aspect, the invention provides a purification method which, proceeding from a cell culture supernatant, results in a VLP-containing composition having a VLP purity of at least 80%, preferably at least 90%, in particular at least 95%, or most preferably at least 99%, and is thereby superior to the previous VLP purification methods. Purity of the VLPs here is meant the relative fraction of the VLPs of the entire mixture of matter as a result of the purification method. This VLP composition is free from PEG and/or salts and is preferably PEG-free.

In a preferred embodiment of the invention, the VLPs substantially or exclusively consist of the VP1 capsid protein which is derived from the capsid protein VP1 of human polyoma virus JC (JCV) or is identical thereto. The sequence of the VP1 of human polyoma virus JC is reproduced in SEQ. ID. NO. 1.

For production of recombinant VP1 in insect cells, according to the invention a nucleic acid can be used which has been optimized for expression in such cells. For example, the sequence shown in SEQ. ID. NO. 2, or a sequence complementary thereto, a sequence corresponding to this sequence in the context of degeneracy of the genetic code, or a sequence hybridizing therewith under stringent conditions can be used. For this purpose the nucleic acid sequence or a recombinant vector containing this sequence is introduced into a suitable host cell, the host cell is cultured under conditions in which the nucleic acid sequence is expressed and the protein is isolated from the cell or the cell supernatant. Stringent hybridization conditions are preferably defined according to Sambrook et al. (1989) Molecular Cloning A Laboratory Manual, Second Edition, Cold Spring Harbor Laboratory Press, and comprise a wash step of 30 min in 0.1×SSC, 0.5% SDS at 60° C. and preferably 68° C.

In the context of the present invention, therefore, a VP1 polypeptide is preferably used which has the amino acid sequence according to SEQ. ID. NO. 3, an amino acid sequence at least 70% identical thereto, preferably at least 80%, particularly preferably at least 90%, and most preferably at least 95% identical thereto, wherein the identity is determined over the entire range of SEQ ID NO. 3.

In a further embodiment, a VP1 protein is used in which the amino acid sequence has been modified in the N-terminal region, e.g. in the region of the 25 N terminal amino acids. In this case, a heterologous nuclear localization signal is preferably introduced into the amino acid sequence of the VP1. Preferred nuclear localization signals contain the amino acid sequence CPGAAPX1X2P, wherein X1 and X2 are any desired amino acids and preferably are each K, and are based, e.g., on the nuclear localization signals of SV40 or BKV. The amino acid sequences of particularly preferred nuclear localization signals are disclosed in EP 2 036 980 A1, which is hereby incorporated in entirety by the present application.

The VP1 produced by recombinant expression is preferably expressed in eukaryotic cells, and particularly preferably in insect cells.

In a further embodiment, a VP2 protein (SEQ ID NO. 6), a VP3 protein (SEQ ID NO. 10), an L1 protein (SEQ ID NO. 13), or an L2 protein (SEQ ID NO. 15) is used.

For the recombinant expression, the wild-type nucleic acid sequences can be used, thus, for example, for VP2 the SEQ ID NO. 4, for VP3 the SEQ ID NO. 8, for L1 the SEQ ID NO. 12 and for L2 the SEQ ID NO. 14.

In a further embodiment, the nucleic acid sequences are codon-optimized for the corresponding expression system. In a particular embodiment, for expression in insect cells, the following nucleic acid sequences are used for expression: SEQ ID NO. 2 for a VP1 protein, SEQ ID NO. 5 for a VP2 protein, SEQ ID NO. 7 for a VP2-HA protein, SEQ ID NO. 9 for a VP3-HA protein.

In a particular embodiment, the respective protein N terminal or C terminal is modified in such a manner that the use as vaccines is improved. In a particular embodiment, a C-terminal localized peptide is concerned, which comprises the hemogluttinin epitope (abbreviated as "HA"). Examples of a protein modified in such a manner are the protein VP2-HA (SEQ ID NO. 7) and the protein VP3-HA (SEQ ID NO. 11).

In a preferred embodiment, cells of *Spodoptera frugiperda* are used, such as, for example, the SF9 cell line, the SF21 cell line or the SF158 cell line, for recombinant expression of the capsid proteins VP1, VP2, VP2-HA, VP3-HA, L1 or L2 and thereby for provision of VLPs. Other insect cell lines can also be used such as, e.g., *Trichoplusia ni* TN-368, IAL-TND1, *Lymantria dispar* IPLB-LdFB, *Mamestra brassica* IZD-MB0503, *L. dispar* IPLB-LdElta, *Anticarsa gemmatalis* UFL-AG286, *Plodia interpunctella* IAL-PID2, *Plutella xylostella* BCIRL-PxHNU3, *T. ni* BTI-TN5B1-4 (HiFive®), *Manduca sexta* MRRL-CH1, *Heliothis virescens* lines: IPLB-HvT1, IPLB-HvE1A, IPLB-HvE6A, and the *Diabrotica undecimpunctata* cell line IPLB-DU182A.

The VLPs according to the invention can be used for diagnostic and therapeutic purposes, e.g. for diagnosis, prevention and treatment of diseases and disease conditions. For this purpose, they can either contain therapeutically active substances, or else alternatively be used without enclosed substances.

In a preferred embodiment, the disease is an infection which was caused by the JC virus, such as PML for instance.

Example 1

Production of a Baculovirus "Seed Strain"

1. Production of the Recombinant Bacmid

The codon-optimized sequence according to SEQ. ID. NO. 2 of the VP1 gene was cloned in pFastBac1 plasmids from GENEART. The plasmid pFastBac1 was transformed in DH5alfa *E. coli* cells, the bacterial cells were grown and the bacteria were stored as glycerol stock at −80° C. The pFasBac-VP1 Plasmid was transformed for multiplication of the Baculo-DNA in DH10Bac *E. coli* cells.

1.1. Transformation of the DH10Bac *E. coli* bacteria

To revitalize the DH10Bac *E. coli* bacteria, the Max Efficiency DH10Bac *E. coli* cells are withdrawn from the ultra-low temperature cabinet (−80° C.), thawed on ice, and 100 µl aliquots of the bacteria are withdrawn and transferred to a 10 ml sample tube.

1.2. The DH10Bac *E. coli* cells are mixed with 1 ng (=1 µL) of pFasBac-VP1 Plasmid and incubated for 30±3 min on ice. The bacteria are transformed with the plasmid DNA pFastBac1-VP1.

1.3. The recombinant VP1-Baculo-DNA is isolated as per standard methods.

2. Revitalizing the Cryo-Conserved SF9 Cells

To revitalize the SF9 cells, a cryotube of the SF9 cells is taken off from the nitrogen storage tank and thawed. After the end of the thawing process, the cells in the 15 ml sample tube are evenly distributed by careful inverting three times and an aliquot taken off for determining the cell count and vitality (living cell count).

After completion of the thawing process, the cells are transferred into a cell culture flask of suitable size (T75 or T175), in such a manner that a cell density of $3 \times 10^5$ of vital cells per milliliter is achieved. In the case of a T75, the cell suspension is adjusted to a volume of ≤30 ml, in the case of a T175 cell culture flask, the cell suspension is adjusted to a volume of >30 ml and ≤50 ml of complete medium and transferred to the cell culture flask. For expansion, the SF9 cells are incubated in an incubator at a temperature of 26° C. and an atmospheric humidity of ≥80%.

3. Expansion of the Cells

The cells are incubated in the incubator until the cell lawn has a density of above 70%. Then, the cells are detached from the bottom of the cell culture vessel and distributed onto a larger cell culture flask, or a plurality of cell culture flasks. For this purpose, the cells in the cell culture flask are rinsed with PBS buffer and detached from their growth surface using the cell scraper. For uniform distribution of the cells in the complete medium, the culture vessel is carefully whirled and then an aliquot is taken off for cell counting. In the renewed seeding, in each case $1 \times 10^6$ cells/well are inoculated into 3 ml of complete medium.

4. Transfection of the Insect Cells with Recombinant VP1-Baculo-DNA-Cellfectin Complexes 16 to 24 hours after seeding the cells into 6 well plates, the cell culture vessel is withdrawn from the incubator, the complete medium is taken off and per well, 1 ml of preheated, serum-free medium is added.

Then, the DNA-Cellfectin complexes are produced. For this purpose, 8 µl of Cellfectin reagent are mixed with 100 µl of serum-free medium. 2 µg (=2 µL) of VP1-Baculo-DNA is diluted with serum-free medium. The Cellfectin batch is combined with the VP1-Baculo-DNA batch and incubated for 30±2 min at room temperature (20±4° C.). 210 µl of the Cellfectin-DNA transfection batches are pipetted into each well of the 6 well plate, and the cells are incubated in the incubator for 5 hours±15 min at 26±1° C. Then, the medium containing the Cellfectin-DNA transfection batch is withdrawn from the individual wells of the 6 well plate and 2 ml/well of complete medium are added. The transfected cells are further incubated for 72±1 hours at 26±1° C. The recombinant baculoviruses are released into the cell culture medium during this time. For harvesting the recombinant baculoviruses, the virus-containing cell culture medium is withdrawn from the transfected cells and transferred into a 15 ml sample tube and centrifuged for 10 min at 2000×g at 4° C., in order to separate off the cell debris present of the lysed cells from the virus-containing cell culture medium. Then, the virus-containing cell culture medium (the supernatant) is transferred into a 2 ml sample tube and stored at 5±3° C. until further use thereof. The baculoviruses are termed P1. 1 ml thereof is stored at −80±5° C. The remaining volume is stored for production of the seed strain.

5. Production of the Baculovirus Seed Strain 5.1. Preparation of the Sf9 Insect Cells for Baculovirus Production The cells are incubated in the incubator until the cell lawn has a density of greater than 70%. Then, the cells are accordingly detached from the bottom of the cell culture vessel and distributed over a greater growth surface area or a plurality of cell culture flasks. For this purpose, the cells in the cell culture flask are rinsed with PBS buffer and detached from the growth surface thereof using the cell scraper. For uniform distribution of the cells in the complete medium, the culture vessel is carefully whirled and then a sample is taken off for cell count determination. On the basis of the determined cell count, in each case $5 \times 10^6$ cells per T25 cell culture flask are seeded into 5 ml of complete medium.

5.2. Infection of the SF9 Cells with the Recombinant Baculoviruses 16 to 24 hours after seeding the cells, the cell culture flask is removed from the incubator and the complete medium is visually and microscopically examined for turbidity and thus for possible contamination. Then, the complete medium is withdrawn and 4 ml of new preheated complete medium are added thereto. For this purpose, 1 ml of the P1 baculovirus in complete medium is added. During the following infection, the SF9 cells with the recombinant baculoviruses are incubated at 26±2° C. for 3 (±1) days in the incubator.

5.3. Harvest of the Recombinant Baculovirus

For harvesting the produced baculoviruses, the cell culture medium is taken off from the infected cells and transferred to a 15 or 50 ml sample tube and centrifuged for 10 min at 2000×g at 4° C. in order to separate off the cell debris present of the lysed cells from virus-containing medium. Then, the virus-containing cell culture medium (supernatant) is stored at 5 (±3° C.

In order to quantify the titer of the viruses, the baculovirus DNA is isolated from 150 µl of virus-containing medium and amplified and quantitated by means of quantitative PCR. The baculoviruses are termed P2 and stored at −80±5° C.

6. Storage of the Recombinant Baculoviruses

Of P1 and P2, in each case 1 ml is withdrawn twice and transferred to labeled 2 ml cryotubes and stored as reserve samples at −80 (±5° C.

Example 2

Production of VP1-VLPs by Baculovirus-Mediated Expression in SF9 Cells

1. Revitalizing the Cryopreserved SF9 Cells

To revitalize the SF9 cells, a cryotube of the SF9 cells was taken off from the nitrogen storage tank in room B.OG 2.4.06 and thawed. After the end of the thawing process, the cells in 15 ml sample tubes are distributed evenly by careful inversion, and a sample taken off for determining the cell count and vitality (living cell count).

After completion of the thawing process, the cells are transferred to a cell culture flask of suitable size (T75 or T175, suspension flasks 500 ml), in such a manner that a cell density of $3 \times 10^5$ cells per milliliter is reached. The size of the cell culture flask is based upon the count of the frozen cells and vitality thereof after thawing. In the case of a T75, the cell suspension is adjusted to a volume >10 and ≤30 ml, in the case of a T175 cell culture flask, the cell suspension is adjusted to a volume of >30 ml and ≤50 ml of complete medium and transferred to the cell culture flask. For expansion, the SF9 cells are incubated in an incubator at a temperature of 26° C. and an atmospheric humidity of ≥80%.

2. Expansion of the Cells

The cells are incubated in the incubator until the cell lawn has a density of greater than 70%. Then, the cells are rinsed with PBS buffer, detached from the bottom of the cell culture vessel using a sterile cell scraper and distributed into a larger cell culture flask or a plurality of cell culture flasks. For uniform distribution of the cells in the complete medium, the culture vessel is carefully whirled and then a sample is taken off for determining the cell count. The cell count determined establishes in what volume of complete medium the cells are then resuspended and in what size or in what number of cell culture flasks the SF9 cells are transferred. In this case the following applies: in each case $3 \times 10^5$ cells/ml of complete medium are seeded. Wherein 12 to 30 milliliters are transferred into a T75 flask, and 30 to 50 milliliters into a T175 flask, and 300 to 500 ml of cell suspension are transferred into the suspension flask. One day after transferring the SF9 cells into new cell culture flasks, preparation of the SF9 cells for infection with baculoviruses is started.

3. Infection of the SF9 Cells with Baculoviruses
3.1. Preparation of the SF9 Cells for Infection with Baculoviruses Before the actual infection process, the SF9 cells are detached from the growth surface thereof, the count of the vital cells is determined and the cells are transferred to one or more T175 cell culture flasks or to a 500 ml suspension flask. For this purpose, $3 \times 10^7$ cells in 50 ml of complete medium per T175 cell culture flask and 30 to $50 \times 10^8$ per 500 ml suspension flask are seeded into serum-free medium.

3.2. Infection of the SF9 Cells with Baculoviruses 16 to 24 hours after seeding the cells, the cell culture flask is taken out of the incubator, the complete medium is withdrawn and 10 ml of preheated, serum-free medium are added thereto. Then, the cell culture flask is carefully whirled and the serum-free medium withdrawn again. In order that the cell lawn is not dried out, immediately 10 ml of serum-free medium are added and the amount of recombinant baculoviruses in complete medium pipetted in such a manner that a multiplicity of infection (MOI) of 1 is achieved. SF9 suspension cells are infected with the MOI 5 directly into the whole volume. During the following infection, the SF9 cells with the baculoviruses are incubated for 20±5 min at room temperature (20±4° C.). Then, 30 ml of serum-free cell culture medium are added to each T175 cell culture flask and the adherent or suspension cells are incubated for a further 5 (±1) days in the incubator.

4. Harvesting the VP1-VLPs

To harvest the VP1-VLPs, the cell culture medium is taken off from the infected cells and transferred to a 50 ml sample tube and centrifuged for 60 min at 5000×g and 5° C. in order to separate the cell debris present of the lysed cells from the protein-containing medium. Then, the protein-containing cell culture medium (supernatant) is transferred to a suitable glass beaker and stored at 5 (±3° C.

Example 3

Purification of the VP1-VLPs by Means of a Weak Anion Exchanger

1. Purification of the VP1-VLPs by Means of DEAE-FPLC

The VP1-VLPs in the cell culture medium are purified using crossflow filtration (Vivoflow System Easy Load from Sartorius) and also concentrated in the same process step. The crossflow system is prepared for use. 500 ml of ddH$_2$O are placed into a suitable reservoir and the system rinsed therewith. The pressure range is 1.5 to 2.5 bar. 500 ml of 10 mM Tris-HCl is placed in the reservoir, the system is rinsed therewith. The pressure range is 1.5 to 2.5 bar.

The cell culture supernatant is freed from possible cell debris using a centrifugation step. The clarified cell culture supernatant is transferred to the reservoir and pumped through the system. The original volume is reduced to half and then a relatively large reservoir (generally having a volume of 1 to 2 L) is connected to the standard buffer system (10 mM Tris-HCl, 100 mM NaCl). Then, the medium is replaced by Tris-HCl buffer system (10 mM Tris-HCl, 100 mM NaCl). The volume is reduced to 150 ml. By means of this crossflow filtration, all low-molecular-weight contaminants down to proteins and protein fragments having a size of 100 kDa are removed.

In the sample, the VLPs are first present as intact particles. The protein contaminants and free nucleic acids present in the sample are separated off by the following anion-exchange chromatography. In this case, a DEAE-Sepharose column is used as weak ion exchanger. The VLPs are eluted in the standard buffer using a linear NaCl gradient (100 mM to 1 M NaCl) or by stepwise gradients (3 steps: 1. 50 to 150 mM NaCl, 2. 200 to 400 mM NaCl and 3. 1 M to 2 M NaCl; 4 steps: 1. 50 to 150 mM NaCl, 2. 200 to 400 mM NaCl, 3. 500 mM to 800 mM NaCl and 4. 1 M to 2 M NaCl).

2. Optional Secondary Purification by Dialysis

Optionally, the VLP-containing sample is then dialysed for 24±2 hours against 10 mM Tris-HCl, 50 to 150 mM NaCl, pH 7.5 in order to set the correct the salt concentration.

3. Storage of the VP1-VLPs

The VP1-VLPs are diluted to the concentration of 0.5 µg/µl with 10 mM Tris-HCl, 150 mM NaCl, pH 7.5, divided into 1.5 ml sample tube aliquots and stored at −80±5° C.

Example 4

Purification of the VP1-VLPs by Means of a Strong Anion Exchanger

1. Purification of the VP1-VLPs by Means of Q-Sepharose-FPLC

The VP1-VLPs in the cell culture medium are purified with the aid of crossflow filtration (Vivoflow System Easy Load from Sartorius) and also concentrated in the same process step. The crossflow system is prepared for use. 500 ml of ddH$_2$O are placed in an appropriate reservoir and the system is rinsed therewith. The pressure range is 1.5 to 2.5 bar. 500 ml of 10 mM Tris-HCl are placed in the reservoir, the system is rinsed therewith. The pressure range is 1.5 to 2.5 bar.

The cell culture supernatant is freed from possible cell debris using a centrifugation step. The clarified cell culture supernatant is transferred to the reservoir and pumped through the system. The original volume is reduced to half and then a larger reservoir (generally having a volume of 1 to 2 L) is connected to the standard buffer system (10 mM Tris-HCl, 100 mM NaCl). Then, the medium is replaced by Tris-HCl buffer system (10 mM Tris-HCl, 100 mM NaCl). The volume is reduced to 150 mL. By means of this crossflow filtration, all low-molecular-weight contaminants down to proteins and protein fragments having a size of 100 kDa are removed.

In the sample, the VLPs are first present as intact particles. Via the subsequent anion-exchanger chromatography, the protein contaminants present in the sample and free nucleic acids are separated off. In this case, a Q-Sepharose column is used as strong ion exchanger. The VLPs are eluted in the standard buffer using a linear NaCl gradient (100 mM to 1 M NaCl) or by stepwise gradient (3 steps: 1. 50 to 150 mM NaCl, 2. 200 to 400 mM NaCl and 3. 1 M to 2 M NaCl; 4 steps: 1. 50 to 150 mM NaCl, 2. 200 to 400 mM NaCl, 3. 500 mM to 800 mM NaCl and 4. 1 M to 2 M NaCl).

2. Optional Secondary Purification by Means of Dialysis

Optionally, the VLP-containing sample is then dialysed for 24±2 hours against 10 mM Tris-HCl, 50 to 150 mM NaCl, pH 7.5 in order to correct the salt concentration.

3. Storage of the VP1-VLPs

The VP1-VLPs are diluted to the concentration of 0.5 µg/µl using 10 mM Tris-HCl, 150 mM NaCl, pH 7.5, divided into aliquots in 1.5 ml sample tubes and stored at −80±5° C.

Example 5

Purification of the VP1-Pentamers Using a Weak Anion Exchanger

1. Dissociation of the VLPs into VP1-Pentamers

In the first step, the VLPs in the sample are dissociated by adding from 5 to 20 mM DTT and 10-30 mM EGTA (final concentration) at room temperature for 1 hour and applied to a column having a DEAE matrix as weak anion exchanger with a DEAE matrix. This step is substantially to obtain a virtually 100% purity of the VP1 pentamers, since in this step, the packaged nucleic acids and other contaminants are eliminated. The pentamers are eluted using a linear NaCl gradient (100 mM to 1 M NaCl) or by a stepwise gradient (3 steps: 1. 50 to 150 mM NaCl, 2. 200 to 400 mM NaCl and 3. 1 M to 2 M NaCl; 4 steps: 1.50 to 150 mM NaCl, 2. 200 to 400 mM NaCl, 3. 500 mM to 800 mM NaCl and 4. 1 M to 2 M NaCl).

2. Optional Secondary Purification by Dialysis

In the event that a reduction of the salt concentration is necessary, the VP1-pentamer-containing solution can optionally be dialyzed overnight at 5±3° C. against physiological saline. In the event of a packaging of active ingredients, the VP1 pentamers are mixed with the active ingredient without this optional secondary purification step (see following step 3).

3. Mixing the VP1 Pentamers with the Active Ingredients

1 μg to 100 μg of purified VP1 pentamers are mixed with 1 to 10 μg of plasmid DNA. The mixture is incubated for 15 min at room temperature. The mixture is placed in dialysis chambers (for example from Pierce) with pore sizes between 5 kDa and 20 kDa. The dialysis chambers are placed in reassociation buffer.

4. Reassociation of the VP1 Pentamers to Form the VLPs

The VP1 pentamers are reassociated to form the VLPs by dialysis against what is termed reassociation buffer, containing 1 to 5 mM $CaCl_2$, 10 mM Tris-HCl and 150 mM NaCl, pH 7.5 at 5±3° C. for 24-48 h.

5. Storage of the Active Ingredient-Containing VLPs

Thereafter, the VLPs are stored at 5±3° C. until further processing or are frozen for long-term storage at −80° C.

Example 6

Purification of the VP1 Pentamers by Means of a Strong Anion Exchanger

The VP1-VLPs in the cell culture medium are purified using crossflow filtration (Vivoflow System Easy Load from Sartorius) and also concentrated in the same process step. The crossflow system is prepared for use. 500 ml of $ddH_2O$ are placed into an appropriate reservoir and the system is rinsed therewith. The pressure range is 1.5 to 2.5 bar. 500 mL of 10 mM Tris-HCl are placed in the reservoir, the system is rinsed therewith. The pressure range is 1.5 to 2.5 bar.

The cell culture supernatant is freed from cell debris by a centrifugation step. The clarified cell supernatant is transferred to the reservoir and pumped through the system. The original volume is reduced to half and then a larger reservoir (generally having a volume of 1 to 2 L) is connected to the standard buffer system (generally the standard buffer used is 10 mM Tris-HCl, 100 mM NaCl). Then, the medium is replaced by Tris-HCl buffer system (generally the standard buffer used is 10 mM Tris-HCl, 100 mM NaCl). The volume is reduced to 150 mL. This crossflow filtration removes all low-molecular-weight contaminants down to proteins and protein fragments having a size of 100 kDa.

2. Dissociation of the VLPs into VP1 Pentamers

In the first step, the VLPs in the sample are dissociated by adding 5 to 20 mM DTT and 10-30 mM EGTA (final concentration) at room temperature for 1 hour and are applied to a Mono Q column or Q-Sepharose column. This step is essential in order to obtain a virtually 100% purity of the VP1 pentamers, since in this step the packaged nucleic acids and other contaminants are eliminated. The pentamers are eluted using a linear NaCl gradient (100 mM to 1 M NaCl) or by stepwise gradient (3 steps: 1. 50 to 150 mM NaCl, 2. 200 to 400 mM NaCl and 3. 1 M to 2 M NaCl; 4 steps: 1. 50 to 150 mM NaCl, 2. 200 to 400 mM NaCl, 3. 500 mM to 800 mM NaCl and 4. 1 M to 2 M NaCl).

3. Optional Secondary Purification by Means of Dialysis

In the event that reduction of the salt concentration is necessary, the VP1-pentamer-containing solution is optionally dialysed overnight at 5±3° C. against physiological saline. In the event of packaging of active ingredients, the VP1 pentamers are mixed with the active ingredient without this optional secondary purification step (see following step 3).

4. Mixing the VP1 Pentamers with the Active Ingredients

1 μg to 100 μg of the purified VP1 pentamers are mixed with 1 to 10 μg of plasmid DNA. The mixture is incubated for 15 min at room temperature. The mixture is placed in a dialysis chamber (for example from Pierce) having pore sizes between 5 kDa and 20 kDa. The dialysis proceeds against a reassociation buffer.

5. Reassociation of the VP1 Pentamers to Form the VLPs

The VP1 pentamers are reassociated to form the VLPs by dialysis against what is termed a reassociation buffer containing 1 to 5 mM $CaCl_2$, 10 mM Tris-HCl and 150 mM NaCl, pH 7.5) at 5±3° C. over 24-48 h.

6. Storage of the Active Ingredient-Containing VLPs

Thereafter, the VLPs are stored at 5±3° C. until further processing, or, for long-term storage, are frozen at −80° C. or alternatively lyophilized.

ABBREVIATIONS

Bacmid=Shuttle Vector, can be propagated in *E. coli* and in insect cells

FCS=Fetal calf serum

LAF=Laminar Air Flow min=Minutes rpm=Revolutions per minute

RT=Room temperature

T25, T75, T175=Cell culture flask having 25, 75 or 175 $cm^2$ growth area

Complete medium=TC-100 insect medium with 10% fetal calf serum

VLP=Virus-like particle

VP1=Virus Protein 1 of the JC virus

SEQUENCE LISTING

The Sequence Listing associated with this application is filed in electronic form via EFS-Web and is hereby incorporated by reference into this specification in its entirety. The name of the text file containing the Sequence Listing is SequenceListing15JAN2016. The size of the text file is 36,657 Bytes, and the text file was created on Jan. 15, 2016.

The present invention is not limited to embodiments described herein; reference should be had to the appended claims.

The invention claimed is:

1. A method for purifying virus-like particles (VLPs) of human polyomavirus JC (JCV) comprising a structural protein VP1, the method comprising:
   filtering a VLP-containing composition through a filter medium having an exclusion limit of 30 kDa to 1500 kDa;
   dissociating the virus-like particles (VLPs) so as to obtain VP1 pentamers;
   purifying the VP1 pentamers by anion exchange chromatography so as to obtain purified VP1 pentamers; and
   reassociating the purified VP1 pentamers so as to obtain reassociated virus-like particles (VLPs),
   wherein,
   the VLP-containing composition is a supernatant of a culture of VLP-expressing cells (cell culture supernatant),
   a buffer exchange is achieved during the filtering, and before filtration, the cell culture supernatant is not chromatographed.

2. The method as recited in claim 1, wherein the filter medium comprises an exclusion limit of at least 40 kDa.

3. The method as recited in claim 1, further comprising: building up a pressure difference of between 0.5 bar and 10 bar during the filtering.

4. The method as recited in claim 1, wherein, after the filtering, the method further comprises:
   purifying the VLP-containing composition via an additional chromatography.

5. The method as recited in claim 1, wherein the virus-like particles (VLPs) have a structural protein VP1 comprising one of the amino acid sequences encoded by the nucleic acid sequences according to SEQ. ID. NO: 1 or SEQ. ID. NO: 2.

6. The method as recited in claim 2, wherein the exclusion limit is from 80 to 15000 kDa.

7. The method as recited in claim 2, wherein the exclusion limit is about 100 kDa.

8. The method as recited in claim 3, wherein the pressure difference is between 0.5 and 5 bar.

9. The method as recited in claim 3, wherein the pressure difference is between 0.5 and 3 bar.

10. The method as recited in claim 4, wherein the purifying of the VLP-containing composition via the additional chromatography is performed via anion-exchange chromatography.

11. The method as recited in claim 1, wherein a VLP purity is at least 80%.

12. The method as recited in claim 1, wherein a VLP purity is at least 90%.

13. The method as recited in claim 1, wherein a VLP purity is at least 95%.

14. The method as recited in claim 1, wherein a VLP purity is at least 70%.

* * * * *

SEQUENCE LISTING

<160> NUMBER OF SEQ ID NOS: 16

<210> SEQ ID NO 1
<211> LENGTH: 1065
<212> TYPE: DNA
<213> ORGANISM: JC virus
<220> FEATURE:
<221> NAME/KEY: misc_feature
<222> LOCATION: (1)..(1065)
<223> OTHER INFORMATION: capsid protein VP1

<400> SEQUENCE: 1

```
atggcccaa caaaaagaaa aggagaaagg aaggaccccg tgcaagttcc aaaacttctt       60
ataagaggag gagtagaagt tctagaagtt aaaactgggg ttgactcaat tacagaggta     120
gaatgctttt taactccaga aatgggtgac ccagatgagc atcttagggg ttttagtaag     180
tcaatatcta tatcagatac atttgaaagt gactccccaa atagggacat gcttccttgt    240
tacagtgtgg ccagaattcc actacccaat ctaaatgagg atctaacctg tggaaatata   300
ctcatgtggg aggctgtgac cttaaaaact gaggttatag gggtgacaag tttgatgaat   360
gtgcactcta atgggcaagc aactcatgac aatggtgcag gaagccagt gcagggcacc    420 agctttcatt tttttctgt tggggggag gctttagaat tacaggggt gctttttaat      480 tacagaacaa gtacccaga tgaacaatt tttccaaaga atgccacagt gcaatctcaa     540
gtcatgaaca cagagcacaa ggcgtaccta gataagaaca aagcatatcc tgttaatgt    600 tgggttcctg atcccaccag aaatgaaaac acaagatatt ttgggacact aacaggagga   660
gaaaatgttc ctccagttct tcatataaca aacactgcca caaacagtgtt gcttgatgaa 720 tttggtgttg ggccactttg caaggtgac aacttatact tgtcagctgt tgatgtctgt   780
ggcatgttta caacaggtc tggttcccag cagtggagag gactctccag atatttaag    840 gtgcagctaa ggaaaaggag ggttaaaaac ccctacccaa tttctttcct tcttactgat   900
ttaattaaca gaaggactcc tagagttgat gggcagccta tgtatggcat ggatgctcaa   960
gtagaggagg ttagagttttt tgagggaaca gaggagcttc caggggaccc agacatgatg 1020
agatacgttg acaaatatgg acagttgcag acaaaaaatgc tgtaa                    1065
```

<210> SEQ ID NO 2
<211> LENGTH: 1065
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1065)
<223> OTHER INFORMATION: VP1 capsid protein; codon optimized

<400> SEQUENCE: 2

```
atggctccca ccaagcgcaa gggcgagccc aaggaccccg tgcaagtgcc caagctgctg      60
atccgtggtg gtgtcgaggt gctggaagtc aagaccggcg tggactccat taccgaggtg    120
gagtgcttcc tcaccccga gatgggtgac cctgacgagc acctgagggg cttctccaag    180
tccatctcca tctccgacac cttcgagtcc gactccccca accgtgacat gctgccctgc    240
tactccgtgg ctcgtatccc cctgcccaac ctgaacgagg acctgacttg cggcaacatc    300
ctgatgtggg aggctgtgac cctcaagacc gaggtcatcg gcgtgacttc cctgatgaac   360
gtgcactcca acggcaggc tacccacgac aacggtgctg gcaagccgt gcagggaacc      420 tccttccact tcttctccgt gggtggcgag gctctggaac tccagggcgt ggtgttcaac    480
```

```
taccgtacca agtaccccga cggcaccatc ttccccaaga acgctactgt gcagtcccaa      540
gtgatgaaca ccgagcacaa ggcttacctg acaagaaca aggcctaccc cgtggagtgc       600
tgggtgcccg accccacccg taacgagaac acccgttact tcggcaccct gaccggtgga     660
gagaacgtgc cccccgtgct gcacatcacc aacaccgcta ccaccgtgct gctggacgag     720
ttcggtgtcg gtcccctgtg caagggcgac aacctgtacc tgtccgctgt ggacgtgtgc     780
ggcatgttca ccaaccgttc cggttcccag cagtggcgtg gcctgtcccg ctacttcaag     840
gtgcagctgc gcaagcgtcg tgtgaagaac ccctacccta tctccttcct gctgaccgac    900
ctgatcaacc gtcgtacccc tcgtgtggac ggccagccca tgtacggcat ggacgctcag     960
gtggaagagg tccgcgtgtt cgagggcacc gaggaattgc ccggcgaccc cgacatgatg    1020
cgttacgtgg acaagtacgg ccagctccag accaagatgc tgtaa                    1065
```

<210> SEQ ID NO 3
<211> LENGTH: 354
<212> TYPE: PRT
<213> ORGANISM: JC virus
<220> FEATURE:
<221> NAME/KEY: MISC_FEATURE
<222> LOCATION: (1)..(354)
<223> OTHER INFORMATION: capsid protein VP1

<400> SEQUENCE: 3

```
Met Ala Pro Thr Lys Arg Lys Gly Glu Pro Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Arg Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Ser Leu Met Asn Val His Ser Asn Gly Gln Ala Thr
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Val Leu Leu Asp Glu
225                 230                 235                 240

Phe Gly Val Gly Pro Leu Cys Lys Gly Asp Asn Leu Tyr Leu Ser Ala
```

```
                245                 250                 255
Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Lys Tyr Gly Gln Leu Gln Thr Lys
            340                 345                 350

Met Leu

<210> SEQ ID NO 4
<211> LENGTH: 1035
<212> TYPE: DNA
<213> ORGANISM: JC virus
<220> FEATURE:
<221> NAME/KEY: misc_feature
<222> LOCATION: (1)..(1035)
<223> OTHER INFORMATION: cpasid protein VP2

<400> SEQUENCE: 4
atgggtgccg cacttgcact ttttggggac ctagttgcta ctgtttctga ggctgctgct      60
gccacaggat tttcagtagc tgaaattgct gctggagagg ctgctgctac tatagaagtt     120
gaaattgcat cccttgctac tgtagagggg attacaagta cctctgaggc tatagctgct     180
ataggcctta ctcctgaaac atatgctgta ataactggag ctccgggggc tgtagctggg     240
tttgctgcat ggttcaaac tgtaactggt ggtagtgcta ttgctcagtt gggatataga     300
ttttttgctg actgggatca taaagtttca acagttgggc ttttttcagca gccagctatg     360 gctttacaat tatttaatcc agaagactac tatgatattt tatttcctgg agtgaatgcc     420
tttgttaaca atattcacta tttagatcct agacattggg gcccgtcctt gttctccaca     480
atctcccagg cttttttggaa tcttgttaga gatgatttgc cagccttaac ctctcaggaa     540
attcagagaa gaacccaaaa actatttgtt gaaagtttag caaggttttt ggaagaaact     600
acttgggcaa tagttaattc accagctaac ttatataatt atatttcaga ctattattct     660
agattgtctc cagttaggcc ctctatggta aggcaagttg cccaaaggga gggaacctat     720
atttcttttg gccactcata cacccaaagt atagatgatg cagacagcat tcaagaagtt     780
acccaaaggc tagatttaaa accccaaat gtgcaatctg gtgaatttat gaaagaagt     840 attgcaccag gaggtgcaaa tcaaagatct gctcctcaat ggatgttgcc tttactttta     900
gggttgtacg ggactgtaac acctgctctt gaagcatatg aagatggccc caacaaaaag     960
aaaaggagaa aggaaggacc ccgtgcaagt tccaaaactt cttataagag gaggagtaga    1020
agttctagaa gttaa                                                    1035

<210> SEQ ID NO 5
<211> LENGTH: 1062
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
```

<222> LOCATION: (1)..(1062)
<223> OTHER INFORMATION: Capsid protein VP2-HA including haemagglutinin
    epitop tag, codon optimized

<400> SEQUENCE: 5

```
atgggagccg ccctggccct gctgggagat

```
            130                 135                 140

Ile His Tyr Leu Asp Pro Arg His Trp Gly Pro Ser Leu Phe Ser Thr
145                 150                 155                 160

Ile Ser Gln Ala Phe Trp Asn Leu Val Arg Asp Asp Leu Pro Ala Leu
                165                 170                 175

Thr Ser Gln Glu Ile Gln Arg Arg Thr Gln Lys Leu Phe Val Glu Ser
            180                 185                 190

Leu Ala Arg Phe Leu Glu Glu Thr Thr Trp Ala Ile Val Asn Ser Pro
        195                 200                 205

Ala Asn Leu Tyr Asn Tyr Ile Ser Asp Tyr Tyr Ser Arg Leu Ser Pro
    210                 215                 220

Val Arg Pro Ser Met Val Arg Gln Val Ala Gln Arg Glu Gly Thr Tyr
225                 230                 235                 240

Ile Ser Phe Gly His Ser Tyr Thr Gln Ser Ile Asp Asp Ala Asp Ser
                245                 250                 255

Ile Gln Glu Val Thr Gln Arg Leu Asp Leu Lys Thr Pro Asn Val Gln
            260                 265                 270

Ser Gly Glu Phe Ile Glu Arg Ser Ile Ala Pro Gly Gly Ala Asn Gln
        275                 280                 285

Arg Ser Ala Pro Gln Trp Met Leu Pro Leu Leu Gly Leu Tyr Gly
    290                 295                 300

Thr Val Thr Pro Ala Leu Glu Ala Tyr Glu Asp Gly Pro Asn Lys Lys
305                 310                 315                 320

Lys Arg Arg Lys Glu Gly Pro Arg Ala Ser Ser Lys Thr Ser Tyr Lys
                325                 330                 335

Arg Arg Ser Arg Ser Ser Arg Ser
            340

<210> SEQ ID NO 7
<211> LENGTH: 234
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(234)
<223> OTHER INFORMATION: capsid protein VP2-HA including C-terminal
      haemagglutinin epitope tag, codon optimized

<400> SEQUENCE: 7

Met Gly Ala Ala Leu Ala Leu Leu Gly Asp Leu Val Ala Thr Val Ser
1               5                   10                  15

Glu Ala Ala Ala Ala Thr Gly Phe Ser Val Ala Glu Ile Ala Ala Gly
                20                  25                  30

Glu Ala Ala Ala Thr Ile Glu Val Glu Ile Ala Ser Leu Ala Thr Val
            35                  40                  45

Glu Gly Ile Thr Ser Thr Ser Glu Ala Ile Ala Ala Ile Gly Leu Thr
        50                  55                  60

Pro Glu Thr Tyr Ala Val Ile Thr Gly Ala Pro Gly Ala Val Ala Gly
65                  70                  75                  80

Phe Ala Ala Leu Val Gln Thr Val Thr Gly Gly Ser Ala Ile Ala Gln
                85                  90                  95

Leu Gly Tyr Arg Phe Phe Ala Asp Trp Asp His Lys Val Ser Thr Val
            100                 105                 110

Gly Leu Phe Gln Gln Pro Ala Met Ala Leu Gln Leu Phe Asn Pro Glu
        115                 120                 125
```

```
Asp Tyr Tyr Asp Ile Leu Phe Pro Gly Val Asn Ala Phe Val Asn Asn
            130                 135                 140

Ile His Tyr Leu Asp Pro Arg His Trp Gly Pro Ser Leu Phe Ser Thr
145                 150                 155                 160

Ile Ser Gln Ala Phe Trp Asn Leu Val Arg Asp Asp Leu Pro Ala Leu
                165                 170                 175

Thr Ser Gln Glu Ile Gln Arg Arg Thr Gln Lys Leu Phe Val Glu Ser
            180                 185                 190

Leu Ala Arg Phe Leu Glu Glu Thr Thr Trp Ala Ile Val Asn Ser Pro
        195                 200                 205

Ala Asn Leu Tyr Asn Tyr Ile Ser Asp Tyr Tyr Ser Arg Leu Ser Pro
    210                 215                 220

Val Arg Pro Ser Met Val Arg Gln Val Ala
225                 230
```

<210> SEQ ID NO 8
<211> LENGTH: 678
<212> TYPE: DNA
<213> ORGANISM: JC virus
<220> FEATURE:
<221> NAME/KEY: misc_feature
<222> LOCATION: (1)..(678)
<223> OTHER INFORMATION: capsid protein VP3

<400> SEQUENCE: 8

| | | | | |
|---|---|---|---|---|
| atggctttac | aattatttaa | tccagaagac | tactatgata | ttttatttcc tggagtgaat | 60 |
| gcctttgtta | acaatattca | ctatttagat | cctagacatt | ggggcccgtc cttgttctcc | 120 |
| acaatctccc | aggcttttg | gaatcttgtt | agagatgatt | tgccagcctt aacctctcag | 180 |
| gaaattcaga | agaacccca | aaaactattt | gttgaaagtt | tagcaaggtt tttggaagaa | 240 |
| actacttggg | caatagttaa | ttccagct | aacttatata | attatattc agactattat | 300 |
| tctagattgt | ctccagttag | gccctctatg | gtaaggcaag | ttgcccaaag ggagggaacc | 360 |
| tatatttctt | ttggccactc | atacacccaa | agtatagatg | atgcagacag cattcaagaa | 420 |
| gttacccaaa | ggctagattt | aaaaacccca | aatgtgcaat | ctggtgaatt tatagaaaga | 480 |
| agtattgcac | aggaggtgc | aaatcaaaga | tctgctcctc | aatggatgtt gcctttactt | 540 |
| ttagggttgt | acgggactgt | aacacctgct | cttgaagcat | atgaagatgg ccccaacaaa | 600 |
| aagaaaagga | gaaggaagg | accccgtgca | agttccaaaa | cttcttataa gaggaggagt | 660 |
| agaagttcta | gaagttaa | | | | 678 |

<210> SEQ ID NO 9
<211> LENGTH: 705
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(705)
<223> OTHER INFORMATION: capsid protein VP3-HA including haemagglutinin epitop tag, codon optimized

<400> SEQUENCE: 9

| | | | | |
|---|---|---|---|---|
| atggctctgc | agctgttcaa | ccccgaggac | tactacgaca | tcctgttccc cggcgtgaac | 60 |
| gccttcgtga | acaacatcca | ctacctggac | ccccggcact | ggggccctag cctgttctct | 120 |
| acaatcagcc | aggccttctg | gaacctcgtg | cgggacgatc | tgcctgccct gaccagccag | 180 |

| | |
|---|---|
| gaaatccagc ggcggaccca gaaactgttc gtggaaagcc tggcccggtt cctggaagag | 240 |
| acaacctggg ccatcgtgaa cagccccgcc aacctgtaca actacatcag cgactactac | 300 |
| agcagactga gccccgtgcg gcccagcatg gtgcgccagg tggcacagag agagggcacc | 360 |
| tatatcagct tcggccactc ctacacccag agcatcgacg acgccgacag catccaggaa | 420 |
| gtgacccaga gactggacct gaaaaccccc aacgtgcaga gcggcgagtt catcgagaga | 480 |
| tccattgccc ctggcggagc caaccagaga tctgcccctc agtggatgct gcccctgctg | 540 |
| ctgggcctgt acggcacagt gacaccagcc ctggaagcct acgaggacgg ccccaacaag | 600 |
| aagaagcgcc ggaaagaggg ccctagagcc agcagcaaga ccagctacaa gcggcggagc | 660 |
| agaagcagca gatcctaccc atacgatgtt ccagattacg cttga | 705 |

```
<210> SEQ ID NO 10
<211> LENGTH: 225
<212> TYPE: PRT
<213> ORGANISM: JC virus
<220> FEATURE:
<221> NAME/KEY: MISC_FEATURE
<222> LOCATION: (1)..(225)
<223> OTHER INFORMATION: capsid protein VP3

<400> SEQUENCE: 10

Met Ala Leu Gln Leu Phe Asn Pro Glu Asp Tyr Tyr Asp Ile Leu Phe
1               5                   10                  15

Pro Gly Val Asn Ala Phe Val Asn Asn Ile His Tyr Leu Asp Pro Arg
            20                  25                  30

His Trp Gly Pro Ser Leu Phe Ser Thr Ile Ser Gln Ala Phe Trp Asn
        35                  40                  45

Leu Val Arg Asp Asp Leu Pro Ala Leu Thr Ser Gln Glu Ile Gln Arg
    50                  55                  60

Arg Thr Gln Lys Leu Phe Val Glu Ser Leu Ala Arg Phe Leu Glu Glu
65                  70                  75                  80

Thr Thr Trp Ala Ile Val Asn Ser Pro Ala Asn Leu Tyr Asn Tyr Ile
                85                  90                  95

Ser Asp Tyr Tyr Ser Arg Leu Ser Pro Val Arg Pro Ser Met Val Arg
            100                 105                 110

Gln Val Ala Gln Arg Glu Gly Thr Tyr Ile Ser Phe Gly His Ser Tyr
        115                 120                 125

Thr Gln Ser Ile Asp Asp Ala Asp Ser Ile Gln Glu Val Thr Gln Arg
    130                 135                 140

Leu Asp Leu Lys Thr Pro Asn Val Gln Ser Gly Glu Phe Ile Glu Arg
145                 150                 155                 160

Ser Ile Ala Pro Gly Gly Ala Asn Gln Arg Ser Ala Pro Gln Trp Met
                165                 170                 175

Leu Pro Leu Leu Leu Gly Leu Tyr Gly Thr Val Thr Pro Ala Leu Glu
            180                 185                 190

Ala Tyr Glu Asp Gly Pro Asn Lys Lys Arg Arg Lys Glu Gly Pro
        195                 200                 205

Arg Ala Ser Ser Lys Thr Ser Tyr Lys Arg Arg Ser Arg Ser Ser Arg
    210                 215                 220

Ser
225

<210> SEQ ID NO 11
<211> LENGTH: 234
<212> TYPE: PRT
```

```
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(234)
<223> OTHER INFORMATION: capsid protein VP3-HA including C-terminal
      haemagglutinin epitope tag, codon optimized

<400> SEQUENCE: 11
```

Met

```
acacagcggc tggtttgggc ctgtgtaggt gttgaggtag gtcgtggtca gccattaggt      420
gtgggcatta gtggccatcc tttattaaat aaattggatg acacagaaaa tgctagtgct      480
tatgcagcaa atgcaggtgt ggataataga gaatgtatat ctatggatta caaacaaaca      540
caattgtgtt taattggttg caaaccacct ataggggaac actggggcaa aggatcccca      600
tgtaccaatg ttgcagtaaa tccaggtgat tgtccaccat tagagttaat aaacacagtt      660
attcaggatg gtgatatggt tgatactggc tttggtgcta tggactttac tacattacag      720
gctaacaaaa gtgaagttcc actggatatt tgtacatcta tttgcaaata tccagattat      780
attaaaatgg tgtcagaacc atatggcgac agcttatttt tttatttacg aagggaacaa      840
atgtttgtta gacatttatt taatagggct ggtgctgttg gtgaaaatgt accagacgat      900
ttatacatta aaggctctgg gtctactgca aatttagcca gttcaaatta ttttcctaca      960
cctagtggtt ctatggttac ctctgatgcc caaatattca ataaacctta ttggttacaa     1020
cgagcacagg gccacaataa tggcatttgt tggggtaacc aactatttgt tactgttgtt     1080
gatactacac gcagtacaaa tatgtcatta tgtgctgcca tatctacttc agaaactaca     1140
tataaaaata ctaactttaa ggagtaccta cgacatgggg aggaatatga tttacagttt     1200 attttttcaac tgtgcaaaat aaccttaact gcagacgtta tgacatacat acattctatg     1260
aattccacta ttttggagga ctggaatttt ggtctacaac ctcccccagg aggcacacta     1320
gaagatactt ataggtttgt aacatcccag gcaattgctt gtcaaaaaca tacacctcca     1380
gcacctaaag aagatcccct taaaaaatac acttttttggg aagtaaattt aaaggaaaag     1440
ttttctgcag acctagatca gtttcctta ggacgcaaat ttttactaca agcaggattg     1500
aaggccaaac caaatttac attaggaaaa cgaaaagcta cacccaccac ctcatctacc     1560
tctacaactg ctaaacgcaa aaaacgtaag ctgtaa                              1596
```

<210> SEQ ID NO 13
<211> LENGTH: 531
<212> TYPE: PRT
<213> ORGANISM: Human papillomavirus type 16
<220> FEATURE:
<221> NAME/KEY: MISC_FEATURE
<222> LOCATION: (1)..(531)
<223> OTHER INFORMATION: capsid protein L1

<400> SEQUENCE: 13

```
Met Gln Val Thr Phe Ile Tyr Ile Leu Val Ile Thr Cys Tyr Glu Asn
1               5                   10                  15

Asp Val Asn Val Tyr His Ile Phe Phe Gln Met Ser Leu Trp Leu Pro
            20                  25                  30

Ser Glu Ala Thr Val Tyr Leu Pro Pro Val Pro Val Ser Lys Val Val
        35                  40                  45

Ser Thr Asp Glu Tyr Val Ala Arg Thr Asn Ile Tyr Tyr His Ala Gly
    50                  55                  60

Thr Ser Arg Leu Leu Ala Val Gly His Pro Tyr Phe Pro Ile Lys Lys
65                  70                  75                  80

Pro Asn Asn Asn Lys Ile Leu Val Pro Lys Val Ser Gly Leu Gln Tyr
                85                  90                  95

Arg Val Phe Arg Ile His Leu Pro Asp Pro Asn Lys Phe Gly Phe Pro
            100                 105                 110

Asp Thr Ser Phe Tyr Asn Pro Asp Thr Gln Arg Leu Val Trp Ala Cys
        115                 120                 125
```

```
Val Gly Val Glu Val Gly Arg Gly Gln Pro Leu Gly Val Gly Ile Ser
    130                 135                 140

Gly His Pro Leu Leu Asn Lys Leu Asp Asp Thr Glu Asn Ala Ser Ala
145                 150                 155                 160

Tyr Ala Ala Asn Ala Gly Val Asp Asn Arg Glu Cys Ile Ser Met Asp
                165                 170                 175

Tyr Lys Gln Thr Gln Leu Cys Leu Ile Gly Cys Lys Pro Pro Ile Gly
            180                 185                 190

Glu His Trp Gly Lys Gly Ser Pro Cys Thr Asn Val Ala Val Asn Pro
        195                 200                 205

Gly Asp Cys Pro Pro Leu Glu Leu Ile Asn Thr Val Ile Gln Asp Gly
210                 215                 220

Asp Met Val Asp Thr Gly Phe Gly Ala Met Asp Phe Thr Thr Leu Gln
225                 230                 235                 240

Ala Asn Lys Ser Glu Val Pro Leu Asp Ile Cys Thr Ser Ile Cys Lys
                245                 250                 255

Tyr Pro Asp Tyr Ile Lys Met Val Ser Glu Pro Tyr Gly Asp Ser Leu
            260                 265                 270

Phe Phe Tyr Leu Arg Arg Glu Gln Met Phe Val Arg His Leu Phe Asn
        275                 280                 285

Arg Ala Gly Ala Val Gly Glu Asn Val Pro Asp Asp Leu Tyr Ile Lys
290                 295                 300

Gly Ser Gly Ser Thr Ala Asn Leu Ala Ser Ser Asn Tyr Phe Pro Thr
305                 310                 315                 320

Pro Ser Gly Ser Met Val Thr Ser Asp Ala Gln Ile Phe Asn Lys Pro
                325                 330                 335

Tyr Trp Leu Gln Arg Ala Gln Gly His Asn Asn Gly Ile Cys Trp Gly
            340                 345                 350

Asn Gln Leu Phe Val Thr Val Asp Thr Thr Arg Ser Thr Asn Met
        355                 360                 365

Ser Leu Cys Ala Ala Ile Ser Thr Ser Glu Thr Thr Tyr Lys Asn Thr
370                 375                 380

Asn Phe Lys Glu Tyr Leu Arg His Gly Glu Glu Tyr Asp Leu Gln Phe
385                 390                 395                 400

Ile Phe Gln Leu Cys Lys Ile Thr Leu Thr Ala Asp Val Met Thr Tyr
                405                 410                 415

Ile His Ser Met Asn Ser Thr Ile Leu Glu Asp Trp Asn Phe Gly Leu
            420                 425                 430

Gln Pro Pro Pro Gly Gly Thr Leu Glu Asp Thr Tyr Arg Phe Val Thr
        435                 440                 445

Ser Gln Ala Ile Ala Cys Gln Lys His Thr Pro Pro Ala Pro Lys Glu
450                 455                 460

Asp Pro Leu Lys Lys Tyr Thr Phe Trp Glu Val Asn Leu Lys Glu Lys
465                 470                 475                 480

Phe Ser Ala Asp Leu Asp Gln Phe Pro Leu Gly Arg Lys Phe Leu Leu
                485                 490                 495

Gln Ala Gly Leu Lys Ala Lys Pro Lys Phe Thr Leu Gly Lys Arg Lys
            500                 505                 510

Ala Thr Pro Thr Thr Ser Ser Thr Ser Thr Thr Ala Lys Arg Lys Lys
        515                 520                 525

Arg Lys Leu
        530
```

<210> SEQ ID NO 14
<211> LENGTH: 1422
<212> TYPE: DNA
<213> ORGANISM: Human papillomavirus type 16
<220> FEATURE:
<221> NAME/KEY: misc_feature
<222> LOCATION: (1)..(1422)
<223> OTHER INFORMATION: capsid protein L2

<400> SEQUENCE: 14

```
atgcgacaca  acgttctgc   aaaacgcaca  aaacgtgcat  cggctaccca  actttataaa     60
acatgcaaac  aggcaggtac  atgtccacct  gacattatac  ctaaggttga  aggcaaaact    120
attgctgatc  aaatattaca  atatggaagt  atgggtgtat  tttttggtgg  gttaggaatt    180
ggaacagggt  cgggtacagg  cggacgcact  gggtatattc  cattgggaac  aaggcctccc    240
acagctacag  atacacttgc  tcctgtaaga  ccccctttaa  cagtagatcc  tgtgggccct    300
tctgatcctt  ctatagtttc  tttagtggaa  gaaactagtt  ttattgatgc  tggtgcacca    360
acatctgtac  cttccattcc  cccagatgta  tcaggattta  gtattactac  ttcaactgat    420
accacacctg  ctatattaga  tattaataat  actgttacta  ctgttactac  acataataat    480
cccactttca  ctgacccatc  tgtattgcag  cctccaacac  tgcagaaaac  tggagggcat    540
tttacacttt  catcatccac  tattagtaca  cataattatg  aagaaattcc  tatggataca    600
tttattgtta  gcacaaaccc  taacacagta  actagtagca  cacccatacc  agggtctcgc    660
ccagtggcac  gcctaggatt  atatagtcgc  acaacacaac  aagttaaagt  tgtagaccct    720
gcttttgtaa  ccactcccac  taaacttatt  acatatgata  atcctgcata  tgaaggtata    780
gatgtggata  atacattata  ttttctagt   aatgataata  gtattaatat  agctccagat    840
cctgactttt  tggatatagt  tgctttacat  aggccagcat  taacctctag  gcgtactggc    900
attaggtaca  gtagaattgg  taataaacaa  acactacgta  ctcgtagtgg  aaaatctata    960
ggtgctaagg  tacattatta  ttatgatttt  agtactattg  atcctgcaga  agaaatagaa   1020
ttacaaacta  taacaccttc  tacatatact  accactttcac  atgcagcctc  acctacttct   1080
attaataatg  gattatatga  tatttatgca  gatgactta   ttacagatac  ttctacaacc   1140
ccggtaccat  ctgtaccctc  tacatctta   tcaggttata  ttcctgcaaa  tacaacaatt   1200
ccttttggtg  gtgcatacaa  tattcctta   gtatcaggtc  ctgatatacc  cattaatata   1260
actgaccaag  ctccttcatt  aattcctata  gttccagggt  ctccacaata  caattatt    1320
gctgatgcag  gtgacttta   tttacatcct  agttattaca  tgttacgaaa  acgacgtaaa   1380
cgtttaccat  atttttttc   agatgtctct  ttggctgcct  ag                       1422
```

<210> SEQ ID NO 15
<211> LENGTH: 473
<212> TYPE: PRT
<213> ORGANISM: Human papillomavirus type 16
<220> FEATURE:
<221> NAME/KEY: MISC_FEATURE
<222> LOCATION: (1)..(473)
<223> OTHER INFORMATION: capsid protein L2

<400> SEQUENCE: 15

```
Met Arg His Lys Arg Ser Ala Lys Arg Thr Lys Arg Ala Ser Ala Thr
 1               5                  10                  15

Gln Leu Tyr Lys Thr Cys Lys Gln Ala Gly Thr Cys Pro Pro Asp Ile
            20                  25                  30

Ile Pro Lys Val Glu Gly Lys Thr Ile Ala Asp Gln Ile Leu Gln Tyr
        35                  40                  45
```

```
Gly Ser Met Gly Val Phe Phe Gly Gly Leu Gly Ile Gly Thr Gly Ser
        50                  55                  60

Gly Thr Gly Gly Arg Thr Gly Tyr Ile Pro Leu Gly Thr Arg Pro Pro
65                  70                  75                  80

Thr Ala Thr Asp Thr Leu Ala Pro Val Arg Pro Pro Leu Thr Val Asp
                    85                  90                  95

Pro Val Gly Pro Ser Asp Pro Ser Ile Val Ser Leu Val Glu Glu Thr
                100                 105                 110

Ser Phe Ile Asp Ala Gly Ala Pro Thr Ser Val Pro Ser Ile Pro Pro
            115                 120                 125

Asp Val Ser Gly Phe Ser Ile Thr Thr Ser Thr Asp Thr Thr Pro Ala
            130                 135                 140

Ile Leu Asp Ile Asn Asn Thr Val Thr Val Thr Thr His Asn Asn
145                 150                 155                 160

Pro Thr Phe Thr Asp Pro Ser Val Leu Gln Pro Pro Thr Pro Ala Glu
                165                 170                 175

Thr Gly Gly His Phe Thr Leu Ser Ser Ser Thr Ile Ser Thr His Asn
                180                 185                 190

Tyr Glu Glu Ile Pro Met Asp Thr Phe Ile Val Ser Thr Asn Pro Asn
            195                 200                 205

Thr Val Thr Ser Ser Thr Pro Ile Pro Gly Ser Arg Pro Val Ala Arg
210                 215                 220

Leu Gly Leu Tyr Ser Arg Thr Thr Gln Gln Val Lys Val Val Asp Pro
225                 230                 235                 240

Ala Phe Val Thr Thr Pro Thr Lys Leu Ile Thr Tyr Asp Asn Pro Ala
                245                 250                 255

Tyr Glu Gly Ile Asp Val Asp Asn Thr Leu Tyr Phe Ser Ser Asn Asp
            260                 265                 270

Asn Ser Ile Asn Ile Ala Pro Asp Pro Asp Phe Leu Asp Ile Val Ala
            275                 280                 285

Leu His Arg Pro Ala Leu Thr Ser Arg Arg Thr Gly Ile Arg Tyr Ser
            290                 295                 300

Arg Ile Gly Asn Lys Gln Thr Leu Arg Thr Arg Ser Gly Lys Ser Ile
305                 310                 315                 320

Gly Ala Lys Val His Tyr Tyr Tyr Asp Phe Ser Thr Ile Asp Pro Ala
                325                 330                 335

Glu Glu Ile Glu Leu Gln Thr Ile Thr Pro Ser Thr Tyr Thr Thr Thr
            340                 345                 350

Ser His Ala Ala Ser Pro Thr Ser Ile Asn Asn Gly Leu Tyr Asp Ile
            355                 360                 365

Tyr Ala Asp Asp Phe Ile Thr Asp Thr Ser Thr Pro Val Pro Ser
            370                 375                 380

Val Pro Ser Thr Ser Leu Ser Gly Tyr Ile Pro Ala Asn Thr Ile
385                 390                 395                 400

Pro Phe Gly Gly Ala Tyr Asn Ile Pro Leu Val Ser Gly Pro Asp Ile
                405                 410                 415

Pro Ile Asn Ile Thr Asp Gln Ala Pro Ser Leu Ile Pro Ile Val Pro
            420                 425                 430

Gly Ser Pro Gln Tyr Thr Ile Ile Ala Asp Ala Gly Asp Phe Tyr Leu
            435                 440                 445

His Pro Ser Tyr Tyr Met Leu Arg Lys Arg Arg Lys Arg Leu Pro Tyr
450                 455                 460
```

```
Phe Phe Ser Asp Val Ser Leu Ala Ala
465                 470

<210> SEQ ID NO 16
<211> LENGTH: 1140
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1140)
<223> OTHER INFORMATION: VP1 capsid protein; codon optimized; with
      non-coding sequences 5' and 3'

<400> SEQUENCE: 16
cctataaata ttccggatta ttcataccgt cccaccatcg ggcgcggatc cgccaccatg      60
gctcccacca agcgcaaggg cgagcccaag gaccccgtgc aagtgcccaa gctgctgatc    120
cgtggtggtg tcgaggtgct ggaagtcaag accggcgtgg actccattac cgaggtggag    180
tgcttcctca cccccgagat gggtgaccct gacgagcacc tgaggggctt ctccaagtcc    240
atctccatct ccgacacctt cgagtccgac tccccaacc gtgacatgct gccctgctac     300
tccgtggctc gtatccccct gcccaacctg aacgaggacc tgacttgcgg caacatcctg    360
atgtgggagg ctgtgaccct caagaccgag gtcatcggcg tgacttccct gatgaacgtg    420
cactccaacg ccaggctac ccacgacaac ggtgctggca gcccgtgca gggaacctcc      480 ttccacttct ctccgtggg tggcgaggct ctggaactcc agggcgtggt gttcaactac     540
cgtaccaagt accccgacgg caccatcttc cccaagaacg ctactgtgca gtcccaagtg    600
atgaacaccg agcacaaggc ttacctggac aagaacaagg cctacccgt ggagtgctgg     660 gtgcccgacc ccaccgtaa cgagaacacc cgttacttcg gcaccctgac cggtggagag    720
aacgtgcccc ccgtgctgca catcaccaac accgctacca ccgtgctgct ggacgagttc    780
ggtgtcggtc ccctgtgcaa gggcgacaac ctgtacctgt ccgctgtgga cgtgtgcggc    840
atgttcacca accgttccgg ttcccagcag tggcgtggcc tgtcccgcta cttcaaggtg    900
cagctgcgca agcgtcgtgt gaagaacccc taccctatct ccttcctgct gaccgacctg    960
atcaaccgtc gtaccccgtc gtggacggc cagcccatgt acggcatgga cgctcaggtg    1020
gaagaggtcc gcgtgttcga gggcaccgag gaattgcccg cgaccccga catgatgcgt    1080 tacgtggaca agtacggcca gctccagacc aagatgctgt aactgcagtc tcgaggcatg    1140
```